(12) United States Patent
Oh et al.

(10) Patent No.: US 6,369,212 B1
(45) Date of Patent: Apr. 9, 2002

(54) CYTOCHROME P450 GENE HIGHLY EXPRESSED IN THE INCOMPATIBLE INTERACTION

(75) Inventors: Boung-Jun Oh; Moon Kyung Ko; Young Soon Kim, all of Kwangju (KR)

(73) Assignee: Korea Kumbo Petrochemical Co., Ltd., Seoul (KR)

( * ) Notice: Subject to any disclaimer, the term of this patent is extended or adjusted under 35 U.S.C. 154(b) by 0 days.

(21) Appl. No.: 09/499,302

(22) Filed: Feb. 7, 2000

(51) Int. Cl.[7] .................. C07H 21/02; C07H 21/04; C12P 21/06; C12N 1/20; C12N 15/00
(52) U.S. Cl. .............. 536/23.6; 435/252.3; 435/320.1; 435/69.1; 536/23.1
(58) Field of Search .................. 536/23.1, 23.6; 435/252.3, 320.1, 69.1

(56) References Cited

PUBLICATIONS

Oh et al., Molecular Plant–Microbe Interactions, 12, 1044–1052, Dec. 1999.*

* cited by examiner

Primary Examiner—Rebecca E. Prouty
Assistant Examiner—Maryam Monshipouri
(74) Attorney, Agent, or Firm—Jacobson Holman, PLLC

(57) ABSTRACT

The present invention related to a cDNA clone, designated to PepCYP (pepper cytochrome P450 gene) and individual component; thereof including its coding region and its gene product; modification thereto; application of said gene, coding region and modification thereto; DNA construct, vectors and transformed plants each comprising the gene or part thereof.

2 Claims, 6 Drawing Sheets

CYTOCHROME P450 GENE HIGHLY EXPRESSED IN THE INCOMPATIBLE INTERACTION

BACKGROUND OF THE INVENTION

The present invention related to a CDNA clone, designated to PepCYP (pepper cytochrome P450 gene) and individual component; thereof including its coding region and its gene product; modification thereto; application of said gene, coding region and modification thereto; DNA construct, vectors and transformed plants each comprising the gene or part thereof

*Colletotrichum gloeosporioides* (Penz.) is the casual agent of anthracnose diseases on fruit crops (Daykin 1984; Dodd et al. 1991; Prusky et al. 1991) such as pepper (*Capsicum annuum* L.) (Kim et al. 1986; Manandhar et al. 1995). The infection of *C. gloeosporioides* is achieved through conidium germination and formation of appressorium and infection hyphae which are necessary for subsequent cuticular penetration (Bailey et al. 1992). In the avocado-*C. gloeospoioides* interaction, conidium germination and appressorium formation were similar on both unripe-resistant and ripe-susceptible fruits (Prusky and Saka 1989; Prusky et al. 1991). In the pepper and *C. capsici* pathosystem, germination and appressorium formation were higher on the unripe-resistant pepper fruit than on the ripe-susceptible fruit (Adikaram et al. 1983). The germination of *C. musae* was similar on both ripe-susceptible and unripe-resistant banana fruits, but the appressorium formation was stimulated on the unripe fruit (Swinburne 1976). Taken together, in these pathosystems, although conidium germination and appressorium formation are a prerequisite to infect the host plant, they may not be important factors to determine resistant or susceptible interactions between the host fruit of pre- or post-ripening stages and the Colletotrichum fungus. In contrast, plant responses to fungal morphogenesis during fruit ripening may be more important to determine resistant or susceptible interactions.

In Colletotrichum fungi, the topography of the plant surface was thought to be a physical signal for inducing appressorium formation (Staples and Macko 1980). The surface wax of avocado fruit was reported to act as a chemical signal for appressorium formation in *C. gloeosporioides* (Podila et al. 1993). In addition, the genes expressed during the appressorium formation of *C. gloeosporioides* induced by the host surface wax were cloned (Hwang and Kollatukudy 1995). However, plant responses to the conidium germination and appressorium formation of *C. gloeosporioides* have not been studied.

In a previous study, we found that an isolate of *C. gloeosporioides* showed an incompatible interaction with the ripe-red pepper fruit and a compatible interaction with the unripe-mature-green fruit (Oh et al. 1998), even though ripe fruits are generally susceptible to pathogen infection (Prusky et al. 1991; Swinburn 1983). In this pathosystem, higher levels of appressorium and infection hypha formation, and longer infection hypha were observed on the unripe fruit than on the ripe fruit in the early fungal infection step (Kim et al. 1999). A typical sunken necrosis was detected only in the unripe fruit, but not in the ripe fruit at 5 days after inoculation. Based on these data of the fungal morphogenesis and symptom development, we studied the gene expression in the pepper-*C. gloeosporioides* interaction.

By using a mRNA differential display method, we isolated several cDNAs that are differentially induced in the ripe fruit, but not in the unripe fruit after fungal infection. In this study, we report the characterization of one of these cDNAs encoding cytochrome P450 protein (PepCYP). To our knowledge, PepCYP is the first cytochrome P450 gene that accumulates to high levels in an incompatible plant-fungus interaction. The expression of PepCYP gene was examined based on fungal behaviors in the initial infection process and on symptom development during the differential interactions. We found that the PepCYP gene is induced by wounding or exogenous jasmonic acid during ripening. A possible role of the PepCYP in pepper fruits against pathogen infection during ripening is proposed.

SUMMARY OF THE INVENTION

The present invention relates to a cDNA clone, designated to a pepper cytochrome P450 gene, PepCYP, the sequence of which is depicted in SEQ ID No. 1. The anthracnose fungus, *Colletotrichum gloeosporioides*, was previously shown to have an incompatible interaction with ripe-red fruit of pepper (*Capsicum annuum*). However, the fungus had a compatible interaction with unripe-mature-green fruit. By using mRNA differential display, we isolated and characterized a PepCYP gene expressed in the incompatible interaction. The PepCYP gene encodes a protein SEQ ID NO:2 homologous to cytochrome P450 proteins containing a heme-binding domain. The expression level of PepCYP is higher in the incompatible interaction than in compatible interaction, and then remains elevated in the incompatible interaction. However, in the compatible interaction the expression of PepCYP is transient. The induction of PepCYP gene is up-regulated by wounding or jasmonic acid treatment during ripening. Analysis of PepCYP expression by in situ hybridization shows that the accumulation of PepCYP mRNA is localized in the epidermal cell layers, but not in the cortical cell layers. An examination of transverse sections of the fruits inoculated with the fungus shows that the fungus invades and colonizes the epidermal cell layers of the unripe fruit at 24 h and 72 h after inoculation, respectively, but not those of the ripe fruit. These results suggest that the PepCYP gene product plays a role in the defense mechanism when the fungus invades and colonizes the epidermal cells of fruits in the incompatible interaction during the early fungal infection process. The PepCYP gene can be cloned into an expression vector to produce a recombinant DNA expression system suitable for insertion into cells to form a transgenic plant transformed with these genes. In addition, the PepCYP gene of this invention can be also used to produce transgenic plants that exhibit enhanced resistance against phytopathogens, including fungi, bacteria, viruses, nematode, mycoplasmalike organisms, parasitic higher plants, flagellate protozoa, and insects.

BRIEF DESCRIPTION OF THE DRAWINGS

FIG. 2. Alignment of the deduced amino acid sequence from PepCYP cDNA (pepper) (Genbank AF122821) with other cytochrome P450 proteins from potato (CYPs.ch), soybean (CYP71D8), avocado (CYP71A1), catmint (CYP71A5), Arabidopsis (CYP71B6), and tobacco (hsr515). The upper line indicates the hydrophobic N-terminal membrane anchor region of PepCYP (amino acid residues 1 to 27). The conserved PFGXGXRXCXG (SEQ ID NO: 3) heme-binding domain in the C-terminal region of the polypeptide is indicated by dots.

DETAILED DESCRIPTION OF THE INVENTION

The present invention has identified a cDNA clone, designated to PepCYP, from the incompatible interaction between pepper and the pepper anthracnose fungus *Colletotrichum gloeosporioides* using mRNA differential display and cDNA library screening.

Figure 1:
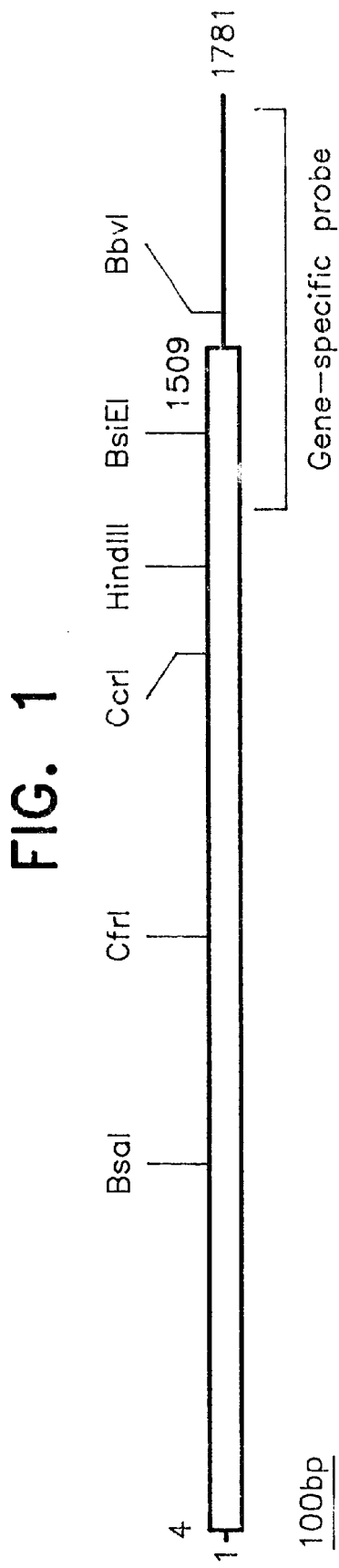
FIG. 1. Restriction enzyme map of a cytochrome P450 cDNA, PepCYP, from pepper (*Capsicum annuum*). Numbers indicate nucleotide positions, and the open bar indicates the coding region that is 4 to 1509 nucleotide positions. The 3' region of PepCYP clone contains the nucleotide sequence of the cDNA fragment, pddICC6, amplified by differential display. This partial cDNA fragment was used for gene-specific RNA probe for in situ hybridization.
Figure 2A:
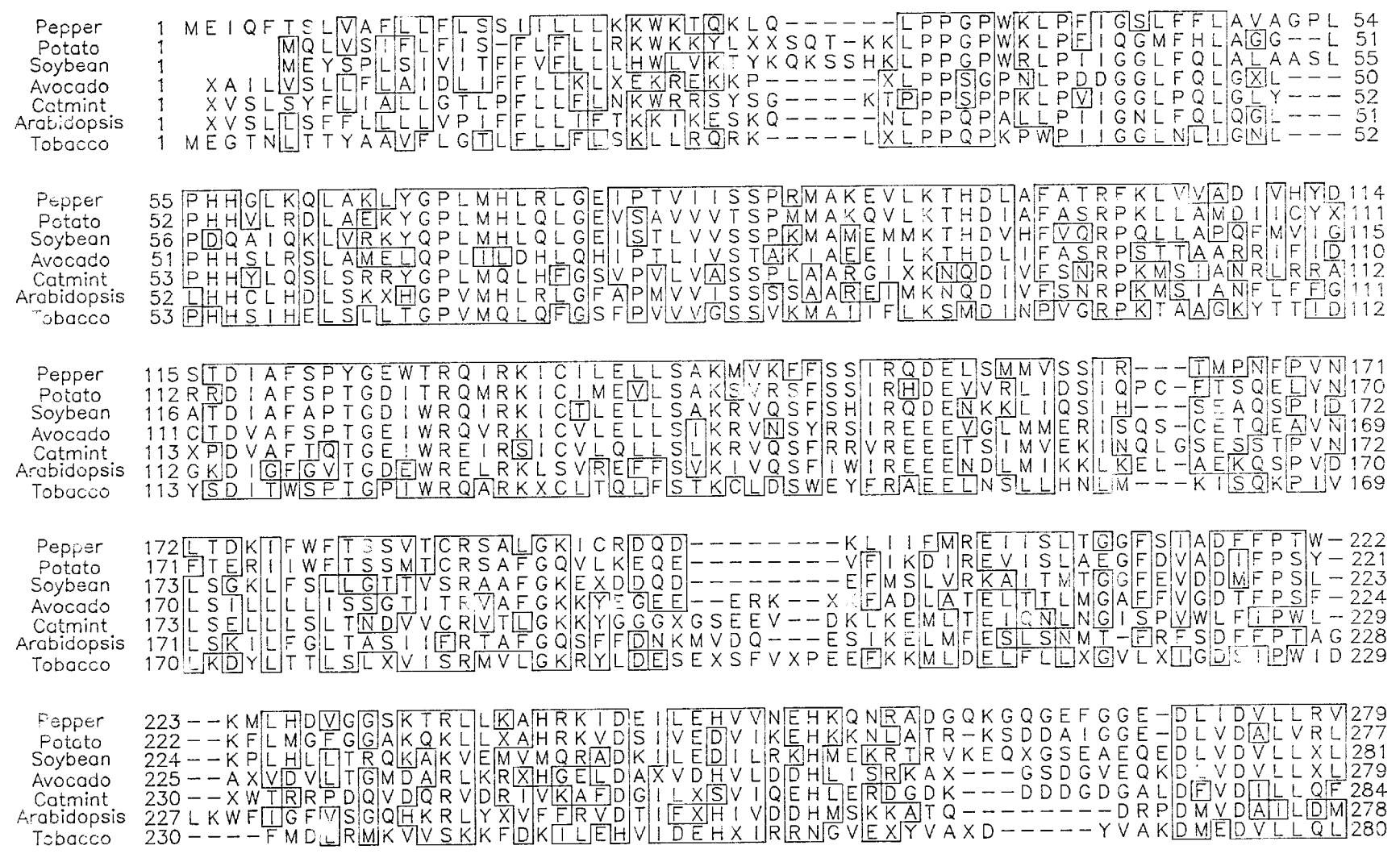

The 1781 bp full-length sequence of PepCYP gene (FIG. 1) contains one open reading frame of 1506 bp from the first translation start (ATG) at nucleotide position 4 to a translational stop (TGA) at position 1509 (Genbank AF122821). The nucleotide sequences of pICC6 encode a polypeptide of 502 amino acids with a calculated molecular mass of 56.8 kDa. A putative polyadenylation site was identified at 22 bp downstream of the stop codon. The amino acid sequence of this cDNA is highly homologous to the genes encoding cytochrome P450s found in plants. Therefore, the pICC6 clone was designated PepCYP for pepper cytochrome P450. The PepCYP protein contains a hydrophobic membrane anchor region in the N terminal region (amino acid residues 1 to 27) (Bozak et al. 1990) (FIG. 2). A heme-binding domain (residues 435 to 440), PFGXGXRXCXG, (SEQ ID NO: 3) is located in the C terminal region of the polypeptide (Frey et al. 1995).

Sequence identity showed that the highest level was 59% with a potato cytochrome P450 protein (CYPs.ch) from a *Solanum chacoense* line rich in glycoalkaloids (Hutvágner et al. 1997) (FIG. 2). Sequence identity was 52% and 48% with CYP71D8 and CYP71D9 from soybean treated with an elicitor, respectively (Schopfer and Ebel 1998). The identities with other CYP71 subfamilies were 46% with avocado CYP71A1 (Bozak et al. 1990), 41% with catmint CYP71A5 (Clark et al. 1997), and 40% with Arabidopsis CYP71B6 (Mizutani et al. 1998). The minimum identity of amino acid sequence required to assign a cytochrome P450 within the same family should be higher than 40% (Nebert et al. 1991). Thus, the pepper gene belongs to the CYP71 family. In the tobacco and phytopathogenic bacterium *Pseudomonas solanacearum* interaction, the first cytochrome P450 gene hsr515 of tobacco that was expressed during the hypersensitive reaction was isolated (Czernic et al. 1996). The hsr515 protein shared 36% identity with the PepCYP.

Figure 3:
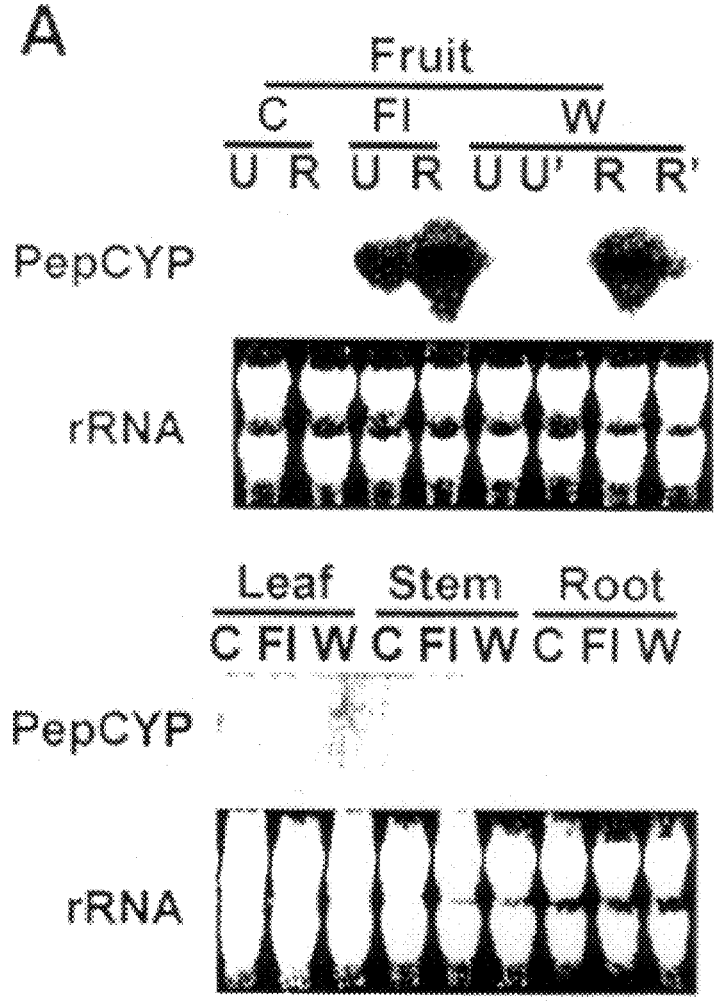
FIG. 3A–3B. A, Expression and induction of PepCYP gene from various organs of pepper by *C. gloeosporioides* inoculation or wounding. RNAs were isolated from the application sites of ripe fruit (R), unripe fruit (U), leaf, stem, and root at 24 h after the treatments of fungal inoculation (FI) or wounding (W). In addition, RNAs of both ripe (R') and unripe fruits (U') at 48 h after wounding were isolated. Ten μl of 5×10⁵ conidium/ml of *C. gloeosporioides* was used for drop-inoculation on various pepper organs. Organs treated with 10μl sterile-water except fungal spores for 24 h were used as the control (C). B, Induction of PepCYP gene from both ripe and unripe fruits of pepper by exogenous abscisic acid (ABA) or jasmonic acid (JA) treatments. RNAs were isolated from the application sites of both ripe (R) and unripe fruits (U) drop-applied with 10 μl of ABA (1=4μM, 2=40 μM) and JA (3=4 μM, 4=40 μM)for 24 h.
Figure 3:
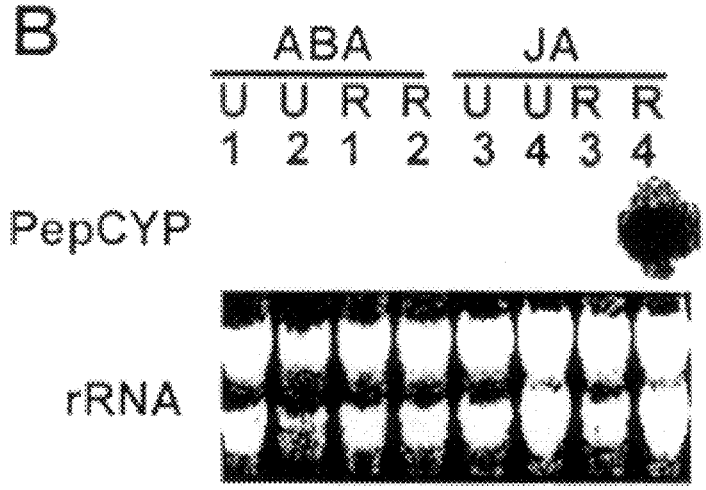

We examined whether the expression of PepCYP gene was fruit-specific by fungal infection or inducible by other treatments. RNA gel blot analysis was performed with total RNAs prepared from fruits, leaves, stems, and roots of the pepper plants at 24 h after fungal inoculation or wounding. The expression of PepCYP gene was observed only in fruits, but not in leaves, stems, and roots after treatments (FIG. 3A). Interestingly, the PepCYP mRNA was induced in both ripe and unripe fruits by fungal infection, but wounding caused the induction of this mRNA only in the ripe fruit.

We further examined whether the wound-inducible PepCYP expression is inducible by ABA or JA treatments. RNA gel blot analysis was performed with total RNAs prepared from the application sites of both ripe and unripe fruits drop-applied with ABA or JA for 24 h. PepCYP mRNA highly accumulated only in the ripe fruit treated with JA at 40 μM (FIG. 3B). However, ABA did not affect the expression of PepCYP in both ripe and unripe fruits. To test whether a high concentration of JA is able to induce the expression of PepCYP in the unripe fruit, JA was applied to the unripe fruit at 100, 400, and 1000 μM. No induction of PepCYP expression was observed in the unripe fruit treated with JA (data not shown).

Figure 4:
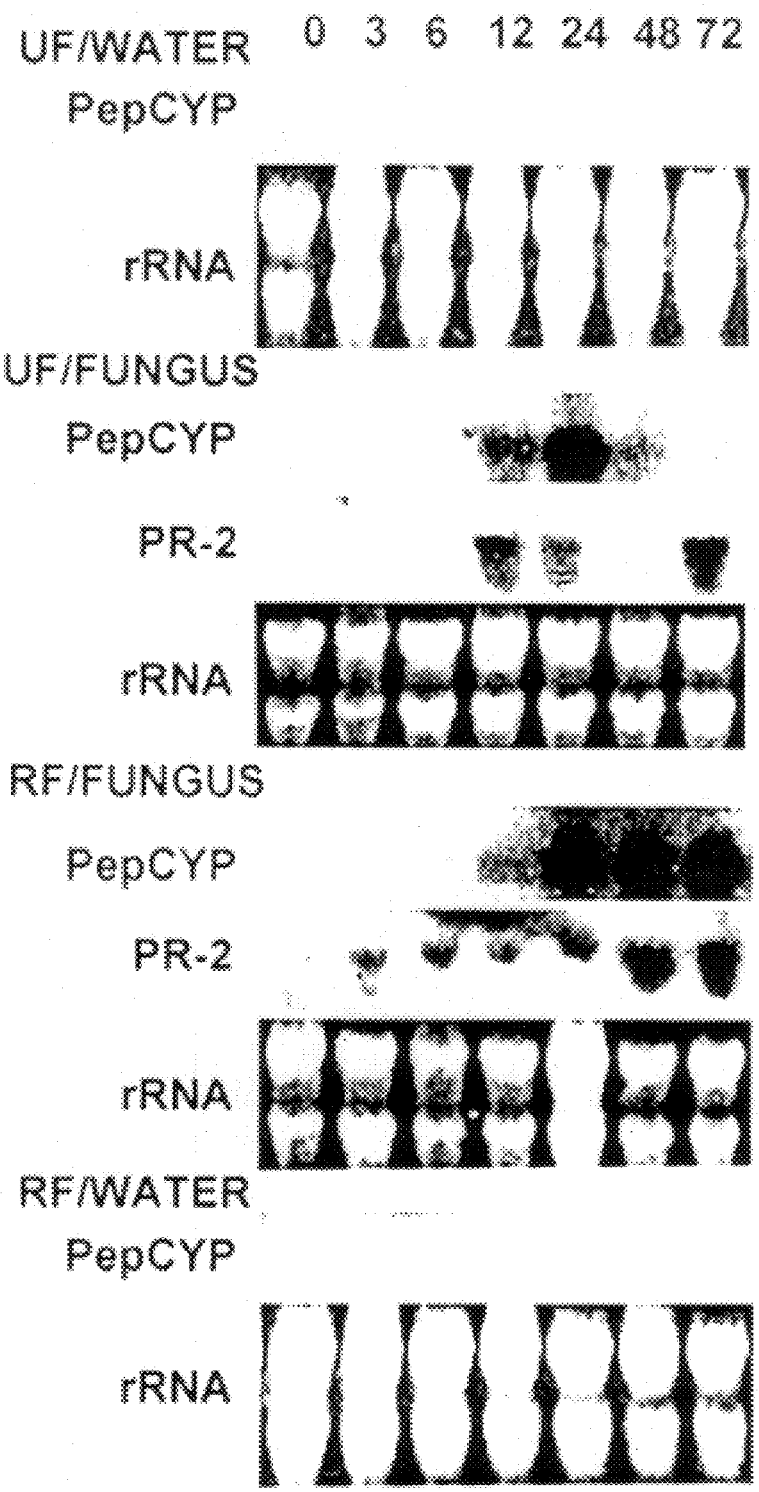
FIG. 4. Differential induction of PepCYP gene from the pepper fruit by *C.gloeosporioides* inoculation. RNAs were isolated from both ripe (RF/FUNGUS—the incompatible interaction) and unripe fruits (UF/FUNGUS—the compatible interaction) after the fungal infection with time-course. Water inoculation without fungal spores on both ripe (RF/WATER) and unripe fruits (UF/WATER) was used as the control. A cDNA for the PR-2 gene was hybridized to the same blot. Numbers indicate in h after inoculation.

We examined whether the induction of time-course of PepCYP mRNA by *C. gloeosporioides* inoculation correlated with fungal morphogenesis and symptom development. RNA gel blot analysis was performed with both unripe and ripe fruits at 0, 3, 6, 12, 24, 48, and 72 HAIs. The PepCYP mRNA was not detected in both ripe and unripe fruits with water inoculation without fungal spores as a control. However, the accumulation of PepCYP mRNA was detected in both ripe and unripe fruits from 12 HAI (FIG. 4). In the unripe fruit, the expression of PepCYP gene is transient and peaks at 24 HAI before rapidly declining to barely detectable levels at 48 and 72 HAI. In contrast, in the ripe fruit, the expression level remains elevated. Thus, the results show that the PepCYP gene is inducible by fungal infection and is differentially expressed in compatible and incompatible interactions.

Figure 5:
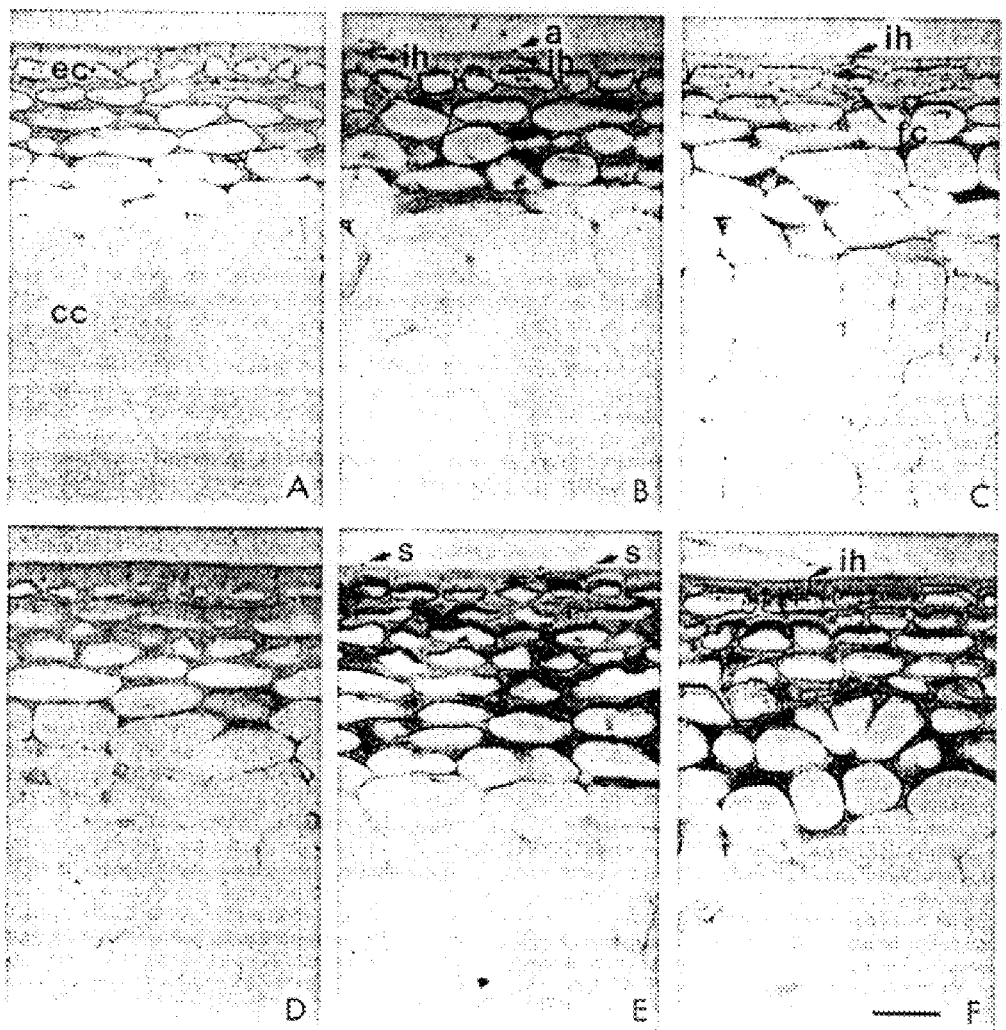
FIG. 5A–5F. In situ localization of PepCYP mRNA in pepper fruits at 24 h and 72 h after inoculation (HAI) with *C. gloeosporioides*. The fungus with infection hypha started to invade in the outer epidermal cells of the unripe fruit at 24 HAI (B), and subsequently colonized the epidermal cells at 72 HAI (C). However, the fungal invasion was rarely observed in the ripe fruit at 24 (E) and 72 HAIs (F). Transverse sections were hybridized with the DIG-labeled antisense RNA probe of pddICC6 as a gene-specific probe. In both uninoculated unripe (A) and ripe fruits (D) used for the controls, transcripts were not detected in the epidermal and cortical cell layers. Deep-blue precipitation of transcripts were detected only in the epidermal cell layers (ec) of both unripe (B) and ripe fruits (E) at 24 HAI, and of the ripe fruit (F) at 72 HAI, but not in the cortical cell layers (cc). Transcripts were not detected in the unripe fruit that was colonized by the fungus at 72 HAI (C). A bar in (F) represents 100 μm. a, appressorium; cc, cortical cell layers; ec, epidermal cell layers; fc, fungal colonization; ih, infection hypha, s; spore.

To examine the localization and accumulation of PepCYP mRNA during early infection, we performed in situ hybridization using a gene-specific antisense or sense RNA probe of pddICC6 (FIG. 1) with sections. The transverse-sections were prepared from the infection sites of both ripe and unripe fruits at 24 and 72 HAIs, respectively. The transcript of PepCYP was not detectable in uninoculated unripe (FIG. 5A) and ripe fruits (FIG. 5D) hybridized with anti-sense or sense RNA probe (data not shown). In unripe fruit, fungus with infection hypha started to invade outer epidermal cells at 24 HAI (FIG. 5B) (Oh et al. 1998). The accumulation of PepCYP mRNA at 24 HAI was localized only in the epidermal cells that were highly vacuolated, but not in the cortical cell layers (FIG. 5B). When the fungus colonized the outer epidermal cells at 72 HAL the induction-level of transcripts was very low or undetectable (FIG. 5C). In ripe fruit, fungal invasion was rarely observed at 24 HAI (FIG. 5E), and even at 72 HAI (FIG. 5F). This result shows that fungal invasion and colonization are inhibited in incompatible-ripe fruit during early infection. The accumulation of the transcripts in the epidermal cells at 24 HAI was sustained up to 72 HAI. These results suggest that the expression of the PepCYP gene is localized to the epidermal cell layers of the ripe fruit during incompatible interaction.

The PepCYP gene can be cloned into an expression vector to produce a recombinant DNA expression system suitable for insertion into cells to form a transgenic plant transformed with these genes. In addition, the PepCYP gene of this invention can be also used to produce transgenic plants that exhibit enhanced resistance against phytopathogens, including fungi, bacteria, viruses, nematode, mycoplasmalike organisms, parasitic higher plants, flagellate protozoa, and insects.

EXAMPLES

Fungal inoculum and plant material

Monoconidial isolate KG13 of *C. gloeosporioides* was cultured on potato dextrose agar (Difco, Detroit, Mich.) for 5 days in darkness at 28° C. Sterile distilled water was added and conidia were harvested through four layers of cheesecloth to remove mycelial debris. Ten $\mu$l of 5×10$^5$ conidium/ml of *C. gloeospioides* was used for drop-inoculation on both ripe and unripe pepper fruits as described (Oh et al. 1998).

Both ripe-red and unripe-mature-green fruits of pepper cv Nokkwang were grown and harvested under greenhouse conditions. For wound treatments, five healthy ripe and unripe fruits were deeply scratched with a knife and incubated at 100% relative humidity at 27° C. in the dark. Ten $\mu$l of ABA at 4 and 40 $\mu$M, or JA at 4 and 40 $\mu$M were drop-applied to both ripe and unripe sets of five fruits, respectively. After incubation under the conditions described above, the fruits were excised to 1 cm$^2$ at the drop-application site for the fungus, ABA or JA, and at the wounding site. The samples were then frozen in liquid nitrogen. Leaf, root, and stem samples were harvested from 3-week-old plants and handled as described above for fungal inoculation and wounding.

mRNA differential display

Total RNA was extracted from healthy or infected ripe and unripe fruits using the RNeasy Plant kit (Qiagen, Hilden, Germany) according to the manufacturer's instructions. We used total RNA as template for the reverse transcriptase reaction and performed differential display with [$\alpha^{33}$P]dATP instead of [$\alpha^{35}$S]dATP (Liang and Pardee 1992). Anchored primers and random-arbitrary primers were purchased from Operon Technologies (Operon, Alameda, Calif.). PCR-amplified cDNA fragments were separated on denaturing 5% polyacrylamide gels in Tris-borate buffer. cDNAs were recovered from the get, amplified by PCR, and cloned into pGEM-T easy vector (Promega, Madison, Wis.) as described (Oh et al. 1995).

Construction and screening of cDNA library

Poly(A)$^+$mRNA was purified from total RNA of unripe-green fruits at 24 and 48 h after inoculation with *C. gloeosporioides* using the Oligotex mRNA Kit (Qiagen). The cDNA library (2.5×10$^5$ plaque-forming unit with a mean insert size of 1.2 kb) was constructed in the cloning vector $\lambda$ZAPII (Stratagene, Heidelburg, Germany) according to the manufacturer's instructions.

A partial cDNA, designated pddICC6, from the differential display analysis was used as a probe to screen the *C. gloeosprioides*-induced pepper cDNA library. After three rounds of plaque hybridization, positive plaques were purified. The pBluescript SK phagemid containing cDNAs was excised in vivo from the ZAP Express vector using the ExAssit helper phage.

DNA sequencing and homology search cDNA sequencing was performed with an ALFexpress automated DNA sequencer (Amersham Pharmacia Biotech, Buckinghamshire, UK). Analysis of nucleotide and amino acid sequences was performed using the DNASIS sequence analysis software for Windows, version 2.1 (Hitachi, San Bruno, Calif.). The multiple sequence alignment was produced with the clustal W program. For a homology search, cDNA sequence was compared to the NCBI non-redundant databases using the BLAST electronic mail server (Altschul et al. 1997).

RNA blot and hybridization

Total RNA (10 $\mu$g/lane) from each plant tissue used in this study was separated on 1.2% denaturing agarose gels in the presence of formaldehyde. RNA gel-blotting, hybridization and washing were conducted as described by the manufacturer of the positively charged nylon membrane employed (Hybond N$^+$; Amersham Pharmacia Biotech). Radiolabeled probes were prepared with [$\alpha$-$^{32}$P]dCTP (Amersham Pharmacia Biotech) using a random primer-labeling kit (Boehringer, Mannheim, Germany).

Tissue preparation and in situ hybridization

Pepper fruits were fixed in 1% glutaraldehyde/2% paraformaldehyde in 100 mM sodium phosphate buffer pH 7.0, dehydrated in ethanol and embedded in paraffin. Tissues were transverse-sectioned at 10 $\mu$m in thickness and stained with DAPI (10 $\mu$g/ml) to examine the infection hypha of the fungus in pepper fruits (Russell et al. 1975).

pddICC6 was used to prepare gene-specific DIG-labeled antisense RNA probes using T7 RNA polymerase or sense RNA probes using sp6 RNA polymerase. Hybridization steps were performed according to the manufacture's recommendation (Boehringer, Mannheim, Germany).

Cloning of a fungal-inducible cytochrome P450 gene of pepper

To isolate genes differentially induced from the ripe fruit but not from the unripe fruit in response to the fungal infection, we used mRNA differential display (Liang and Pardee 1992). Differential display was performed with total RNAs prepared from both unripe and ripe fruits at 24 and 48 h after fungal inoculation. The cDNAs amplified from the ripe fruit were excised from the gel, re-amplified, and cloned. RNA gel blot analysis with these clones was performed to confirm their differential expression. A cDNA clone, named pddICC6 for the incompatible *Capsicum annuum/Colletotrichum gloeosporioides* interaction, hybridized to a transcript of 1.8 kb which accumulated to high levels in the incompatible interaction (data not shown).

In order to isolate the full-length cDNA clone, the insert of pddICC6 was used as a probe for plaque hybridization using a cDNA library prepared from mRNA extracted from the unripe fruit at 24 and 48 h after inoculation with the fungus. A clone containing the longest insert from cDNA library screening was designated pICC6, isolated and sequenced. The 3' region of pICC6 clone contained the nucleotide sequence of pddICC6 as expected.

Sequence analysis and characterization of PepCYP cDNA

The 1781 bp full-length sequence (FIG. 1) contains one open reading frame of 1506 bp from the first translation start (ATG) at nucleotide position 4 to a translational stop (TGA) at position 1509 (GenBank AF122821). The nucleotide sequences of pICC6 encode a polypeptide of 502 amino acids with a calculated molecular mass of 56.8 kDa. A putative polyadenylation site was identified at 22 bp downstream of the stop codon. The amino acid sequence of this cDNA is highly homologous to the genes encoding cytochrome P450s found in plants. Therefore, the pICC6 clone was designated PepCYP for pepper cytochrome P450. The PepCYP protein contains a hydrophobic membrane anchor region in the N terminal region (amino acid residues 1 to 27) (Bozak et al. 1990) (FIG. 2). A heme-binding domain (residues 435 to 440), PFGXGXRXCXG, is located in the C terminal region of the polypeptide (Frey et al. 1995).

Sequence identity showed that the highest level was 59% with a potato cytochrome P450 protein (CYPs.ch) from a *Solanum chacoense* line rich in glycoalkaloids (Hutvágner et al. 1997) (FIG. 2). Sequence identity was 52% and 48% with CYP71D8 and CYP71D9 from soybean treated with an elicitor, respectively (Schopfer and Ebel 1998). The identities with other CYP71 subfamilies were 46% with avocado CYP71A1 (Bozak et al. 1990), 41% with catmint CYP71A5 (Clark et al. 1997), and 40% with Arabidopsis CYP71B6 (Mizutani et al. 1998). The minimum identity of amino acid sequence required to assign a cytochrome P450 within the same family should be higher than 40% (Nebert et al. 1991). Thus, the pepper gene belongs to the CYP71 family. In the tobacco and phytopathogenic bacterium *Pseudomonas solanacearum* interaction, the first cytochrome P450 gene hsr515 of tobacco that was expressed during the hypersensitive reaction was isolated (Czernic et al. 1996). The hsr515 protein shared 36% identity with the PepCYP.

Fruit-specific induction of PepCYP gene by fungal inoculation: up-regulation during ripening, and upon wounding and jasmonic acid treatments

*C. gloeosporioides* causes anthracnose diseases on the fruit of various plant species (Daykin 1984; Dodd et al. 1991; Kim et al. 1986, Manandhar et al. 1995, Prusky et al. 1991). Thus, we examined whether the expression of PepCYP gene was fruit-specific by fungal infection or inducible by other treatments. RNA gel blot analysis was performed with total RNAs prepared from fruits, leaves, stems, and roots of the pepper plants at 24 h after fungal inoculation or wounding. The expression of PepCYP gene was observed only in fruits, but not in leaves, stems, and roots after treatments (FIG. 3A). Interestingly, the PepCYP mRNA was induced in both ripe and unripe fruits by fungal infection, but wounding caused the induction of this mRNA only in the ripe fruit.

Jasmonic acid (JA) is a plant hormone with roles in mechanical wounding responses (Creelman et al. 1992; Creelman and Mullet 1997). ABA is hypothesized to be a key component in wound-signaling cascade leading to the activation of a defense gene (Pena-Cortés et al. 1996; Wasternack and Partheir 1997). Thus, we further examined whether the wound-inducible PepCYP expression is inducible by ABA or JA treatments. RNA gel blot analysis was performed with total RNAs prepared from the application sites of both ripe and unripe fruits drop-applied with ABA or JA for 24 h. PepCYP mRNA highly accumulated only in the ripe fruit treated with JA at 40 $\mu$M (FIG. 3B). However, ABA did not affect the expression of PepCYP in both ripe and unripe fruits. To test whether a high concentration of JA is able to induce the expression of PepCYP in the unripe fruit, JA was applied to the unripe fruit at 100, 400, and 1000 $\mu$M No induction of PepCYP expression was observed in the unripe fruit treated with JA (data not shown).

Differential induction of PCYP gene in compatible and incompatible interactions

In our previous studies (Kim et al. 1999; Oh et al. 1998), higher levels of the appressorium and infection hypha formations were observed on the unripe fruit than on the ripe fruit at 12 h and 24 h after inoculation (HAI), respectively. Initial anthracnose symptoms were detected only on the unripe fruit after 48 HAI, and typical sunken necrosis occurred within 120 HAI. Thus, we examined whether the induction of time-course of PepCYP mRNA by *C. gloeosporioides* inoculation correlated with fungal morphogenesis and symptom development. RNA gel blot analysis was performed with both unripe and ripe fruits at 0, 3, 6, 12, 24, 48, and 72 HAIs. The PepCYP mRNA was not detected in both ripe and unripe fruits with water inoculation without fungal spores as a control. However, the accumulation of PepCYP mRNA was detected in both ripe and unripe fruits from 12 HAI (FIG. 4). In the unripe fruit, the expression of PepCYP gene is transient and peaks at 24 HAI before rapidly declining to barely detectable levels at 48 and 72 HAI. In contrast, in the ripe fruit, the expression level remains elevated. Thus, the results show that the PepCYP gene is inducible by fungal infection and is differentially expressed in compatible and incompatible interactions.

A cDNA for the PR-2 gene from *Nicotiana glutinosa* was hybridized to the same blots to serve as a molecular marker for the activation of plant defense responses. In the unripe fruit, a basal level of PR-2mRNA was not detected, but the accumulation of PR-2mRNA was detected at 12 HAI (FIG. 4). And a biphasic accumulation of PR-2 mRNA was observed at 12 and 72 HAIs. In contrast, in the ripe fruit, a basal level of PR-2 mRNA was detected. The expression of PR-2 gene was rapidly induced in the ripe fruit at 3 HA and reached a maximum at 48 HAI.

Localization of PepCYP mRNA during early infection

To examine the localization and accumulation of PepCYP mRNA during early infection, we performed in situ hybridization using a gene-specific antisense or sense RNA probe of pddICC6 (FIG. 1) with sections. The transverse-sections were prepared from the infection sites of both ripe and unripe fruits at 24 and 72 HAIs, respectively. The transcript of PepCYP was not detectable in uninoculated unripe (FIG. 5A) and ripe fruits (FIG. 5D) hybridized with anti-sense or sense RNA probe (data not shown). In unripe fruit, fungus with infection hypha started to invade outer epidermal cells at 24 HAI (FIG. 5B) (Oh et al. 1998). The accumulation of PepCYP mRNA at 24 HAI was localized only in the epidermal cells that were highly vacuolated, but not in the cortical cell layers (FIG. 5B). When the fungus colonized the outer epidermal cells at 72 HAI, the induction-level of transcripts was very low or undetectable (FIG. 5C). In ripe fruit, fungal invasion was rarely observed at 24 HAI (FIG. 5E), and even at 72 HAI (FIG. 5F). This result shows that fungal invasion and colonization are inhibited in incompatible-ripe fruit during early infection. The accumulation of the transcripts in the epidermal cells at 24 HAI was sustained up to 72 HAI. These results suggest that the expression of the PepCYP gene is localized to the epidermal cell layers of the ripe fruit during incompatible interaction.

Discussion

As a first step to investigate the molecular mechanisms involved in the incompatible interaction between the ripe fruit of pepper and *C. gloeosporioides*, several cDNAs were isolated that were differentially expressed in the ripe fruit by fungal infection, but not in the unripe fruit. In this study with one of these cDNAs, we showed the characterization of the PepCYP gene that encodes a protein homologous to plant cytochrome P450 (Bozak et al. 1990; Frey et al. 1995). Cytochrome P450s in plants are membrane-bound proteins involved in several metabolic pathways related to the defense mechanisms (Maule and Ride 1983; Kessmann et al. 1990). Some genes encoding these proteins are induced by wounding (Batard et al. 1997; Frank et al. 1996). In a plant-phytopathogenic bacterium interaction, the tobacco cytochrome P450 gene, hsr515, was isolated during hypersensitive reaction (Czernic et al. 1996). In this study of a fungal-plant interaction, a pepper cytochrome P450 gene, PepCYP, was differentially expressed in compatible and incompatible interactions. Transcript levels of the two interactions were very different with maintenance of elevated levels in the incompatible interaction and a very substantial reduction in the compatible interaction. Together with the hsr515gene in a bacterial-plant interaction, the isolation of PepCYP in the pepper and fungus interaction suggests a new role for cytochrome P450s in plant-pathogen interactions.

Sequence comparison showed that PepCYP protein shared highest homology to the CYPs.ch from a Solanum chacoense line rich in glycoalkaloids (Hutvágner et al. 1997) as well as CYP71D8 and CYP71D9 from soybean treated with an elicitor (Schopfer and Ebel 1998). A possible role of CYPs.ch was suggested to be involved in the synthesis of stress-inducible metabolites. CYP71D8 and CYP71D9 may have a variety of functional roles in terpenoid metabolism (Christoffersen et al. 1995). The antimicrobial sesquiterpenoid phytoalexin, capsidol (Chavez-Moctezuma and Lozoya-Gloria 1996; Watson and Brooks 1984), was synthesized in pepper challenged with fungus (Ward 1976) and an abiotic elicitor, UV light (Back et al. 1998). Therefore, these data raise the possibility that PepCYP functions in the pepper plant's defense against fungal infection. The expression of PepCYP gene in the pepper fruit in response to fungal inoculation and wounding (FIGS. 3 and 4) supports a possible role of PepCYP involved in the plant's defense mechanism.

The first cytochrome P450, CYP71A, in plants was identified during avocado fruit ripening (Bozak et al. 1990). In this study, a basal level of PepCYP mRNA was not detected in ripe or unripe fruits or other various organs of pepper. However, the induction of PepCYP was detected only in fruit after fungal inoculation (FIG. 3A). In addition, the expression of PepCYP was induced only in ripe fruit by wounding and JA treatment (FIG. 3A and B). Thus, these results suggest that PepCYP is developmentally and fruit-specifically regulated, and the induction is upregulated during fruit ripening in response to wounding and JA. JA is reported to have roles in mechanical wounding responses (Creelman et al. 1992; Creelman and Mullet 1997) and in activating genes for plant disease resistance (Johnson et al. 1989; Xu et al. 1994; Reinbothe et al. 1994). However, the role of JA during the fruit ripening has not been well studied, in contrast to ethylene (Theologis 1992). A few cases that methyl JA triggers the ripening process of climacteric fruits including tomato and apple with ethylene production were reported (Czapski and Saniewski 1992; Saniewski et al. 1987a, 1987b). However, the role of JA in nonclimacteric fruits such as pepper, grape and strawberry has not been reported.

Fruit ripening represents a genetically synchronized developmental process unique to plants. Generally, ripe fruit is accompanied by an increased susceptibility to pathogen infection (Prusky et al. 1991; Swinburn 1983). As one of the reproductive organs of the plants, the fruit must be protected from pathogens or abiotic stresses. PR proteins and several antifungal proteins that are responsible for the protection against pathogens during fruit ripening have been identified (Fils-Lycaon et al. 1996; Meyer et al. 1996; Salzman et al. 1998; Tattersall et al. 1997). In the present study, the expression of PepCYP gene was detected only in the ripe fruit after fungal inoculation or wounding. We propose that the PepCYP gene is involved in the defense mechanism for the ripe fruit in order to maintain fruit integrity and to protect seed maturation against biotic and abiotic stresses.

Initial and mature infection hypha of *C. gloeosporioides* developed on pepper fruits at 12 and 24 HAIs, respectively (Oh et al. 1998). PepCYP mRNA in the fruit started to accumulate from 12 HAI and increased at 24 HAI (FIG. 4). Thus, it is likely that PepCYP gene expression occurs when the fungus directly invades the fruit by infection hypha. In microscopic and in situ hybridization observations, although cells didn't directly contact with the fungus, the induction of PepCYP transcript was detected throughout the epidermal cell layers. This result suggests that transcripts are induced by plant-derived defense signals generated after the fungus invasion. On the other hand, the accumulation of PR-2 mRNA in the ripe fruit at 3 HAI when the fungus germinates suggests that this gene is induced early in the incompatible interaction by fungal elicitors rather than plant-derived signals. The induction of PepCYP and PR-2 mRNAs was observed to be higher and faster, respectively, in the incompatible interaction than in the compatible interaction. These similar phenomena have been reported for many other plant-pathogen interactions (Ebrahim-Nesbat et al. 1989; 1993). Thus, higher and faster expression of many defense genes including PepCYP and PR-2 may confer disease resistance for the ripe fruit against fungal infection.

In summary, the present study showed that active fungal invasion and colonization processes are suppressed in the incompatible-interacting ripe fruit. Notably, PepCYP mRNA accumulated to higher levels in the ripe fruit in response to the fungal infection. The transcript is mainly localized in the epidermal cell layers of the pepper fruit after the fungal inoculation. We suggest that the PepCYP gene product plays a critical role in the plant's defense mechanism against the fungal invasion and colonization of the epidermal cells of the fruit in the incompatible interaction. It remains to be elucidated how the cytochrome P450 protein provides an effective defense against the fungal infection in pepper.

REFERENCES

Adikaram, N. K. B., Brown, A. E., and Swinburne, T. R. 1983. Observations on infection of *Capsicum annuum* fruit by *Glomerella cingulata* and *Colletotrichum capsici*. Trans. Brit. Mycol. Soc. 80:395401.

Altschul, S. F., Madden, T. L., Schäffer, A. A., Zhang, J., Zhang, Z., Miller, W, and Lipman, D. J. 1997. Gapped BLAST and PSI-BLAST: a new generation of protein database search programs. Nucleic Acids Res. 25:3389–3402.

Back, K., He, S., Kim, K. U., and Shin, D. H. 1998. Cloning and bacterial expression of sesquiterpene cyclase, a key branch point enzyme for the synthesis of sesquiterpenoid phytoalexin capsidiol in UV-challenged leaves of *Capsicum annuum*. Plant Cell Physiol. 39:899–904.

Bailey, J. A., O'Connell, R. J., Pring, R. J., and Nash, C. 1992. Infection strategies of Colletotrichum species.

Pages 88–120 in: Colletotrichum Biology, Pathology and Control. J. A. Bailey and J. A. Jeger, eds. CAB International, Wallingford, UK.

Batard, Y, Schalk, M., Pierrel, M. A., Zimmerlin, A., Durst, F., and Werck-Reichhart, D. 1997. Regulation of the cinnamate 4-hydroxylase (CYP73a1) in Jerusalem artichoke tubers in response to wounding and chemical treatments. Plant Physiol. 113:951–959.

Bozak, K. R., Yu, H., Sirevåg, R., and Christoffersen, R. E. 1990. Sequence analysis of ripening-related cytochrome P-450 cDNAs from avocado fruit. Proc. Natl. Acad. Sci. USA 87:3904–3908.

Chavez-Moctezuma, M. P, and Lozoya-Gloria, E. 1996. Biosynthesis of the sesquiterpene phytoalexin capsidiol in elicited root cultures of chili pepper (*Capsicum annuum*). Plant Cell Rep. 15:360–366.

Christoffersen, R. E., Percival, F. W and Bozak, K. 1995. Functional and DNA sequence divergence of the CYP71 gene family in higher plants. Pages 207–219 in: Drug metabolism and drug interactions. F. Durst, and D. R O'Keefe, eds. Freund, UK.

Clark, I. M., Forde, B. G., and Hallahan, D. L. 1997. Spatially distinct expression of two new cytochrome P450s in leaves of *Nepeta racemosa*: identification of a trichome-specific isoform. Plant Mol. Biol. 33:875–885.

Creelman, R. A., and Mullet, J. E. 1997. Biosynthesis and action ofjasmonates in plants. Annu. Rev. Plant Physiol. Plant Mol. Biol. 48:355–381.

Creelman, R. A., Tierney, M. L., and Mullet, J. E. 1992. Jasmonic acid/methyl jasmonate accumulate in wounded soybean hypocotyls and modulate wound gene expression. Proc. Natl. Acad. Sci. USA 89:4938–4941.

Czapski, J., and Saniewski, M. 1992. Stimulation of ethylene production and ethylene-forming enzyme in fruits of the non-ripening nor and rin tomato mutants by methyl jasmonate. J. Plant Physiol. 139:265–268.

Czernic, P., Huang, H. C., and Marco, Y 1996. Characterization of hsr201 and hsr515, two tobacco genes preferentially expressed during the hypersensitive reaction provoked by phytopathogenic bacteria. Plant Mol. Biol. 31:255–265.

Daykin, M. E. 1984. Infection in blueberry fruit by *Colletotrichum gloeosporioides*. Plant Dis. 68:984–950.

Dodd, J. C., Estrada, A., Matcham, A., Jeffries, P., and Jeger, M. J. 1991. The effect of environmental factors on *Colletotrichum gloeosporioides*, the causal agent of mango anthracnose, in the Philippines. Plant Pathol. 40:568–575.

Ebrahim-Nesbat, F., Behnke, S., Kleinhofs, A., and Apel, K. 1989. Cultivar-related differences in the distribution of cell-wall bound thionins in compatible and incompatible interactions between barley and powdery mildew. Planta 179:203–210.

Ebrahim-Nesbat, F., Bohl, S., Heitefiss, R., and Apel, K. 1993. Thionin in cell walls and papillae of barley in compatible and incompatible interactions with *Erysiphe graminis* f sp. *hordei*. Physiol. Mol. Plant Pathol. 43:343–352.

Fils-Lycaon, B. R., Wiersma, P. A., Eastwell, K. C., and Sautiere, P. 1996. A cherry protein and its gene, abundantly expressed in ripening fruit, have been identified as thaumatin-like Plant Physiol. 111:269–273.

Frank, M. R., Deyneka, J. M., and Schuler, M. A. 1996. Cloning of wound-induced cytochrome P450 monooxygenase expressed in pea. Plant Physiol. 110: 1035–1046.

Frey, M., Kliem, R., Saedler, H., and Gierl, A. 1995. Expression of a cytochrome P450 gene family in maize. Mol. Gen. Genet. 246:100–109.

Giovannoni, J. J. 1993. Molecular biology of fruit developmental and ripening. Pages 253–287 in: Methods in Plant Molecular Biology. J. Bryant, ed. Academic Press, NY, USA.

Hutvágner, G., Barta, E., and Banfalvi, Z. 1997. Isolation of sequence analysis of a cDNA and related gene for cytochrome P450 proteins from *Solanum chacoense*. Genel 88:247–252.

Hwang, C-S, and Kolattukudy, P. E. 1995. Isolation and characterization of genes expressed uniquely during appressorium formation by *Colletotrichum gloeosporioides* conidia induced by the host surface wax. Mol. Gen. Genet. 247:282–294.

Johnson, R., Narváez, J., An, G., and Ryan, C. 1989. Expression of proteinase inhibitors I and II in transgenic tobacco plants: Effects on natural defense against *Manduca sexta* larvae. Proc. Natl. Acad. Sci. USA 86:9871–9875.

Kessmann, H. Choudhary, A. D., and Dixon, R. A. 1990. Stress response in alfalfa (*Medicago saliva* L.). III. Induction of medicarpin and cytochrome P450 enzyme activities in elicitor-treated cell suspension cultures and protoplasts. Plant Cell Rep. 9:38–41.

Kim, K. D., Oh, B. J., and J. Yang. 1999. Differential interactions of a *Colletotrichum gloeosporioides* isolate with green and red pepper fruits. Phytoparasitica 27:1–10.

Kim, W G., Cho, E. K., and Lee, E. J. 1986. Two strains of *Colletotrichum gloeosporioides* Penz. causing anthracnose on pepper fruits. Korean J. Plant Pathol. 2:107–113.

Liang, P., and Pardee, A B. 1992. Differential display of eukaryotic messenger RNA by means of the polymerase chain reaction. Science 257:967–971.

Manandhar, J. B., Hartman, G. L., and Wang, T. C. 1995. Conidial germination and appressorial formation of *Colletotrichum capsici* and *C. gloeosporioides* isolates from pepper. Plant Dis. 79:361–366.

Maule, A. J., and Ride, J. P. 1983. Cinnamate 4-hydroxylase and hydroxycinnamate: CoA ligase in wheat leaves infected with *Botrytis cinereae*. Phytochemistry 22:1113–1116.

Meyer, B., Houlné, G., Pozueta-Romero, J., Schantz, M-L., and Schantz, R. 1996. Fruit-specific expression of a defensin-type gene family in bell pepper. Upregulation during ripening and upon wounding. Plant Physiol. 112:615–622.

Mizutani, M., Ward, E., and Ohta, D. 1998. Cytochrome P450 superfamily in *Arabidopsis thaliana*: isolation of cDNAs, differential expression, and RFLP mapping of multiple cytochromes P450. Plant Mol. Biol. 37:39–52.

Nebert, D. W, Ride, J. P., Coon, M. J., Estabrook, R. W, Feyereisen, R., Fuji-Kuriyama, Y., Gonzales, F. J., Guenguerich F. P., Gunsalus, I. C., Johnson, E. F., Loper J. C. Sato, R., Waterman, M. R., and Waxman D. J. 1991. The P450 superfamily: update on new sequences, gene mapping, and recommended nomenclature. DNA Cell Biol. 10:1–14.

Oh, B. J., Balint, D. E., and Giovannoni, J. J. 1995. A modified procedure for PCR-based differential display and demonstration of use in plants for isolation of gene related to fruit ripening. Plant Mol. Biol. Rep. 13:70–81.

Oh, B. J., Kim, K. D., and Kim, Y. S. 1998. A microscopic characterization of the infection of green and red pepper fruits by an isolate of *Colletotrichum gloeosporioides*. J. Phytopathol. 146:301–303.

Pena-Cortés, H., Prat, S., Atzorn, R, Wasternack, C., and Willmitzer, L. 1996. Abscisic acid-deficient plants do not accumulate proteinase inhibitor II following systemin treatment. Planta 198:447451.

Podila, G. K., Rogers, L. M., and Kolattukudy, P. E. 1993. Chemical signals from avocado surface wax trigger germination and appressorium formation in *Colletotrichum gloeosporioides*. Plant Physiol. 103:267–272.

Prusky, D., Plumbley, R. A., and Kobiler, I. 1991. The relationship between the antifungal diene levels and fungal inhibition during quiescent infections of *Colletotrichum gloeosporioides* in unripe avocado fruits. Plant Pathol. 40:45–52.

Prusky, D., and Saka, H. 1989. The role of epicuticular wax of avocado fruit in appressoria formation of *Colletotrichum gloeosporioides*. Phytoparasitica 17:140.

Reinbothe, S., Reinbothe, C., Lehman, J., Becker, W, Apel, K., and Parthier, B. 1994. JIP60, a methyl jasmonate-induced ribosome-inactivating protein involved in plant stress reactions. Proc. Natl. Acad. Aci. USA 91:7012–7016.

Russell, W C., Newman, C., and Williamson, D. H. 1975. A simple cytochemical technique for demonstration of DNA in cells infected with mycoplasmas and viruses. Nature 253:461–462.

Salzman, R. A., Tikhonova, I., Bordelon, B. P., Hasegawa, P. M., and Bressan, R. A. 1998. Coordinate accumulation of antifungal proteins and hexoses constitutes a developmentally controlled defense response during fruit ripening in grape. Plant Physiol. 117:465–472.

Saniewski, M., Czapski, J., Nowacki, J., and Lange, E. 1987. The effect of methyl jasmonate on ethylene and 1-amino-cyclopropane-l-carboxylic acid production in apple fruits. Biol. Plant 29:199–203.

Saniewski, M., Nowacki, J., and Czapski, J. 1987. The effect of methyl jasmonate on ethylene production and ethylene-forming enzyme activity in tomatoes. J. Plant Physiol. 129:175–180.

Schopfer, C. R., and Ebel, J. 1998. Identification of elicitor-induced cytochrome P450s of soybean (*Glycine macx L.*) using differential display of mRNA. Mol. Gen. Genet. 258:315–322.

Staples, R. C., and Macko, V 1980. Formation of infection structures as a recognition response in fungi. Exp. Mycol. 4:2–16.

Swinburne, T. R. 1976. Stimulants of germination and appressoria formation by *Colletotrichum musae* (Berk. & Curt.) Arx. in banana leachate. Phytopathol. Z 87:74–90.

Swinburne. T. R. 1983. Post-Harvest Pathology of Fruits and Vegetables. Academic Press, NY, USA.

Tattersall, D. B., van Heeswijck, R., and Bordier, Hoj P. 1997. Identification and characterization of a fruit-specific, thaumatin-like protein that accumulates at very high levels in conjunction with the onset of sugar accumulation and berry softening in grapes. Plant Physiol. 114:759–769.

Theologis, A. 1992. One rotten apple spoils the whole bushel: the role of ethylene in fruit ripening. Cell 70:181–184.

Ward, E. W. B. 1976. Capsidiol production in pepper leaves in incompatible interactions with fungi. Phytopathology 66:175–176.

Wasternack, C., and Partheir, B. 1997. Jasmonate-signaled plant gene expression. Trends Plant Sci. 2:302–307.

Watson, D. G., and Brooks, C. J. 1984. Formation of capsidiol in *Capsicum annuum* fruits in response to non-specific elicitors. Physiol. Plant Pathol. 24:331–337.

Werk-Reichart, D. 1995. Cytochrome P450 in phenylpropanoid metabolism. Pages 171–187 in: Drug metabolism and drug interactions. F. Durst, and D P. O'Keefe, eds. Freund, UK.

Xu, Y, Chang, P-F. L., Liu, D., Narasimhan, M. L., Raghothama, K. G., Hasegawa, P. M., and Bressan, R. A. 1994. Plant defense genes are synergistically induced by ethylene and methyl jasmonate. Plant Cell 6:1077–1085.

What is claimed is:

1. An isolated nucleic acid molecule encoding the pepper cytochrome P450 protein (PepCYP) having the amino acid sequence of SEQ ID NO: 2.

2. The isolated nucleic acid molecule according to claim 1, wherein said nucleic acid molecule is a cDNA molecule having the nucleotide sequence of SEQ ID NO: 1.

* * * * *

SEQUENCE LISTING

```
<160> NUMBER OF SEQ ID NOS: 10

<210> SEQ ID NO 1
<211> LENGTH: 1781
<212> TYPE: DNA
<213> ORGANISM: Capsicum annuum

<400> SEQUENCE: 1
tgaatggaga ttcaattcac caacttagtt gcgttttgc tctttctctc cagcatcatt      60
cttctactca aaaaatggaa aacccaaaag ctaaacttac ctcctggtcc atggaaatta    120 cctttattg gaagcctaca tcacttggca gtggcaggtc cacttcctca tcatggccta    180 aaaatctag caaaacttta tgggccgctc atgcacttac gactcgggga aattcctacc    240
gtcatcattt cgtccccgcg aatggcgaag gaagtactaa aaactcacga cctcgctttc    300
gcaacgaggc cgaaacttgt ggtggctgac atcgtccatt atgatagtac ggatatagca    360
ttttctccat atggtgaata ctggaggcag attcgtaaaa tttgcatact cgaactcctt    420
agtgccaaga tggtcaaatt ctttagctca attcgccagg atgagctgtc gatgatggtc    480
tcatctatac gaaccatgcc aaattttccc gtcaaccttca cagacaaaat attttggttt    540
acaagttcgg taacttgtag atcagctctg ggaaaaatat gtcgtgacca agacaaactg    600
ataattttca tgagggaaat aatatcattg acaggtggat ttagtattgc tgattttttc    660
```

-continued

```
cctacatgga aaatgctaca tgatgttggt ggttcaaaaa ctagactgct gaaggctcat    720
cgtaaaatcg atgagatttt ggaacatgta gtgaatgagc acaaacagaa tcgagcggat    780
ggccaaaagg gtaatggcga atttggcggt gaagatttga tcgatgtttt gctaagggtt    840
cgagaaagtg gagaagttca aatttccatc acggatgaca atatcaaatc aatattagtg    900
gacatgttct ccgctggatc tgaaacgtca tcgacaacta taatttgggc attagctgaa    960
atgatgaaga aaccaagtgt tctagcaaag gcacaagctg aagtgagaca agtcttgaag   1020 gaaagaaag gttttcaaca aattgatctt gatgagttga agtacttgaa gttagtaatc    1080
aaagaaactc taaggatgca ccctccaatt cctctattag tccctagaga atgtatgaag   1140
gatacaaaga ttgacgggta caatatacct ttcaaaactc gagtcatagt taatgcatgg   1200
gcaattggac gagatcctga agttgggat gaccctgaaa gcttttcccc agagagattc    1260
gagaatagtt ctgttgactt tcttggaagc catcatcaat ttattccatt tggtgcggga   1320
agaaggattt gtcctggaat gcttttttggt ttagccaatg ttggacaacc attagctcaa   1380
ttactttatc acttcgatcg gaaactccct aatggacaaa gtcacgaaaa tttgacatg    1440 acggagtcac ctggaatttc tgcaacaaga aaggatgatc ttgttttgat gccacccct    1500 tatgatcctt gaatgtattg agacagttgt agaaataaaa aagagggaga aaatagaaat   1560
ggatgctgct tccaggtcat ttttgttggg agaaatttca aacttcatca acgtaactat   1620
atatagtgtt tgctagagtt ggtttattta ccactctata tcgtatttgg tgtactcaat   1680
aaattgtttg gtgtattata ttacagataa tggattttca ttttcatgtt aaaaaaaaaa   1740
aaaaaaaaaa aaaaaaaaaa aaaaaaaaaa aaaaaaaaa a                        1781
```

<210> SEQ ID NO 2
<211> LENGTH: 502
<212> TYPE: PRT
<213> ORGANISM: Capsicum annuum

<400> SEQUENCE: 2

```
Met Glu Ile Gln Phe Thr Asn Leu Val Ala Phe Leu Leu Phe Leu Ser
  1               5                  10                  15

Ser Ile Ile Leu Leu Leu Lys Lys Trp Lys Thr Gln Lys Leu Gln Leu
             20                  25                  30

Pro Pro Gly Pro Trp Lys Leu Pro Phe Ile Gly Ser Leu Phe Phe Leu
         35                  40                  45

Ala Val Ala Gly Pro Leu Pro His His Gly Leu Lys Gln Leu Ala Lys
     50                  55                  60

Leu Tyr Gly Pro Leu Met His Leu Arg Leu Gly Glu Ile Pro Thr Val
 65                  70                  75                  80

Ile Ile Ser Ser Pro Arg Met Ala Lys Glu Val Leu Lys Thr His Asp
                 85                  90                  95

Leu Ala Phe Ala Thr Arg Phe Lys Leu Val Val Ala Asp Ile Val His
            100                 105                 110

Tyr Asp Ser Thr Asp Ile Ala Phe Ser Pro Tyr Gly Glu Trp Thr Arg
        115                 120                 125

Gln Ile Arg Lys Ile Cys Ile Leu Glu Leu Leu Ser Ala Lys Met Val
    130                 135                 140

Lys Phe Phe Ser Ser Ile Arg Gln Asp Glu Leu Ser Met Met Val Ser
145                 150                 155                 160

Ser Ile Arg Thr Met Pro Asn Phe Pro Val Asn Leu Thr Asp Lys Ile
                165                 170                 175
```

-continued

```
Phe Trp Phe Thr Ser Ser Val Thr Cys Arg Ser Ala Leu Gly Lys Ile
                180                 185                 190
Cys Arg Asp Gln Asp Lys Leu Ile Ile Phe Met Arg Glu Ile Ile Ser
            195                 200                 205
Leu Thr Gly Gly Phe Ser Ile Ala Asp Phe Phe Pro Thr Trp Lys Met
        210                 215                 220
Leu His Asp Val Gly Gly Ser Lys Thr Arg Leu Leu Lys Ala His Arg
225                 230                 235                 240
Lys Ile Asp Glu Ile Leu Glu His Val Val Asn Glu His Lys Gln Asn
                245                 250                 255
Arg Ala Asp Gly Gln Lys Gly Gln Gly Glu Phe Gly Gly Glu Asp Leu
            260                 265                 270
Ile Asp Val Leu Leu Arg Val Arg Glu Ser Gly Glu Val Gln Ile Ser
        275                 280                 285
Ile Thr Asp Asp Asn Ile Lys Ser Ile Leu Val Asp Met Phe Ser Ala
        290                 295                 300
Gly Ser Glu Thr Ser Ser Thr Thr Ile Ile Trp Ala Leu Ala Glu Met
305                 310                 315                 320
Met Lys Lys Pro Ser Val Leu Ala Lys Ala Gln Ala Glu Val Arg Gln
                325                 330                 335
Val Leu Lys Glu Lys Lys Gly Phe Gln Gln Ile Asp Leu Asp Glu Leu
            340                 345                 350
Lys Tyr Leu Lys Leu Val Ile Lys Glu Thr Leu Arg Met His Pro Pro
        355                 360                 365
Ile Pro Leu Leu Val Pro Arg Glu Cys Met Lys Asp Thr Lys Ile Asp
        370                 375                 380
Gly Tyr Asn Ile Pro Phe Lys Thr Arg Val Ile Val Asn Ala Trp Ala
385                 390                 395                 400
Ile Gly Arg Asp Pro Glu Ser Trp Asp Pro Glu Ser Phe Ser Pro
                405                 410                 415
Glu Arg Phe Glu Asn Ser Ser Val Asp Phe Leu Gly Ser His His Gln
            420                 425                 430
Phe Ile Pro Phe Gly Ala Gly Arg Arg Ile Cys Pro Gly Met Lys Phe
        435                 440                 445
Gly Leu Ala Asn Val Gly Gln Pro Leu Ala Gln Leu Leu Tyr His Phe
        450                 455                 460
Asp Arg Lys Leu Pro Asn Gly Arg Ser His Glu Asn Leu Asp Met Thr
465                 470                 475                 480
Glu Ser Pro Gly Ile Ser Ala Thr Arg Lys Asp Asp Leu Val Leu Ile
                485                 490                 495
Ala Thr Pro Tyr Asp Pro
                500
```

```
<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Consensus
      heme-binding domain
<221> NAME/KEY: MOD_RES
<222> LOCATION: (4)
<223> OTHER INFORMATION: variable or unknown amino acid
<221> NAME/KEY: MOD_RES
<222> LOCATION: (6)
<223> OTHER INFORMATION: variable or unknown amino acid
<221> NAME/KEY: MOD_RES
```

```
<222> LOCATION: (8)
<223> OTHER INFORMATION: variable or unknown amino acid
<221> NAME/KEY: MOD_RES
<222> LOCATION: (10)
<223> OTHER INFORMATION: variable or unknown amino acid

<400> SEQUENCE: 3

Pro Phe Gly Xaa Gly Xaa Arg Xaa Cys Xaa Gly
 1               5                   10

<210> SEQ ID NO 4
<211> LENGTH: 502
<212> TYPE: PRT
<213> ORGANISM: Capsicum annuum
<220> FEATURE:
<221> NAME/KEY: MOD_RES
<222> LOCATION: (1)
<223> OTHER INFORMATION: variable or unknown amino acid
<221> NAME/KEY: MOD_RES
<222> LOCATION: (31)
<223> OTHER INFORMATION: variable or unknown amino acid
<221> NAME/KEY: MOD_RES
<222> LOCATION: (224)
<223> OTHER INFORMATION: variable or unknown amino acid
<221> NAME/KEY: MOD_RES
<222> LOCATION: (264)
<223> OTHER INFORMATION: variable or unknown amino acid
<221> NAME/KEY: MOD_RES
<222> LOCATION: (320)
<223> OTHER INFORMATION: variable or unknown amino acid
<221> NAME/KEY: MOD_RES
<222> LOCATION: (470)
<223> OTHER INFORMATION: variable or unknown amino acid

<400> SEQUENCE: 4

Xaa Glu Ile Gln Phe Thr Asn Leu Val Ala Phe Leu Leu Phe Leu Ser
 1               5                   10                  15

Ser Ile Ile Leu Leu Leu Lys Lys Trp Lys Thr Gln Lys Leu Xaa Leu
             20                  25                  30

Pro Pro Gly Pro Trp Lys Leu Pro Phe Ile Gly Ser Leu Phe His Leu
         35                  40                  45

Ala Val Ala Gly Pro Leu Pro His His Cys Leu Lys Asn Leu Ala Lys
     50                  55                  60

Leu Tyr Gly Pro Leu Met His Leu Arg Leu Gly Glu Ile Pro Thr Val
 65                  70                  75                  80

Ile Ile Ser Ser Pro Arg Met Ala Lys Glu Val Leu Lys Thr His Asp
                 85                  90                  95

Leu Ala Phe Ala Thr Arg Pro Lys Leu Val Val Ala Asp Ile Val His
            100                 105                 110

Tyr Asp Ser Thr Asp Ile Ala Phe Ser Pro Thr Gly Glu Ile Trp Arg
        115                 120                 125

Gln Ile Arg Lys Ile Cys Ile Leu Glu Leu Leu Ser Ala Lys Met Val
130                 135                 140

Leu Phe Phe Ser Ser Ile Arg Gln Asp Glu Leu Ser Met Met Val Ser
145                 150                 155                 160

Ser Ile Arg Thr Met Pro Met Pro Phe Pro Val Asn Leu Thr Asp Lys Ile
                165                 170                 175

Phe Trp Phe Thr Ser Ser Val Thr Cys Arg Ser Ala Leu Gly Lys Ile
            180                 185                 190

Cys Arg Asp Gln Asp Lys Leu Ile Ile Phe Met Arg Glu Ile Ile Ser
        195                 200                 205

Leu Thr Gly Gly Phe Ser Ile Ala Asp Phe Pro Thr Trp Lys Xaa
    210                 215                 220
```

Leu Met Asp Val Gly Gly Ser Lys Thr Arg Leu Leu Lys Ala His Arg
225                 230                 235                 240

Lys Ile Asp Glu Ile Leu Glu His Val Val Asn Glu His Lys Gln Asn
            245                 250                 255

Arg Ala Asp Gly Gln Lys Gly Xaa Gly Glu Phe Gly Gly Glu Asp Leu
            260                 265                 270

Ile Asp Val Leu Leu Arg Val Arg Glu Ser Gly Glu Val Gln Ile Ser
            275                 280                 285

Ile Thr Asp Asp Asn Ile Lys Ser Ile Leu Val Asp Met Phe Ser Ala
        290                 295                 300

Gly Ser Glu Thr Ser Ser Thr Thr Ile Ile Trp Ala Leu Ala Met Xaa
305                 310                 315                 320

Met Lys Lys Pro Ser Val Leu Ala Lys Ala Gln Ala Glu Val Arg Gln
            325                 330                 335

Val Leu Lys Glu Lys Lys Gly Phe Gln Gln Ile Asp Leu Asp Glu Leu
            340                 345                 350

Lys Tyr Leu Lys Leu Val Ile Lys Glu Thr Leu Arg Met Met Pro Pro
            355                 360                 365

Ile Pro Leu Leu Val Pro Arg Glu Cys Met Lys Asp Thr Lys Ile Asp
        370                 375                 380

Gly Thr Asn Ile Pro Phe Lys Thr Arg Val Ile Val Asn Ala Asn Ala
385                 390                 395                 400

Ile Gly Arg Asp Pro Glu Ser Trp Asp Pro Glu Ser Phe Ser Pro
            405                 410                 415

Glu Arg Phe Glu Asn Ser Ser Val Asp Phe Leu Gly Ser His His Gln
            420                 425                 430

Phe Ile Pro Phe Gly Ala Gly Arg Arg Ile Cys Pro Gly Met Leu Phe
            435                 440                 445

Gly Leu Ala Asn Val Gly Gln Pro Leu Ala Gln Leu Leu Tyr His Phe
            450                 455                 460

Asp Pro Lys Leu Pro Xaa Gly Gln Ser His Glu Asn Leu Asp Met Thr
465                 470                 475                 480

Glu Ser Pro Gly Ile Ser Ala Thr Arg Lys Asp Asp Leu Val Leu Ile
            485                 490                 495

Ala Thr Pro Tyr Asp Pro
            500

<210> SEQ ID NO 5
<211> LENGTH: 500
<212> TYPE: PRT
<213> ORGANISM: Solanum tuberosum
<220> FEATURE:
<221> NAME/KEY: MOD_RES
<222> LOCATION: (24)..(25)
<223> OTHER INFORMATION: variable or unknown amino acid
<221> NAME/KEY: MOD_RES
<222> LOCATION: (111)
<223> OTHER INFORMATION: variable or unknown amino acid
<221> NAME/KEY: MOD_RES
<222> LOCATION: (236)
<223> OTHER INFORMATION: variable or unknown amino acid
<221> NAME/KEY: MOD_RES
<222> LOCATION: (279)
<223> OTHER INFORMATION: variable or unknown amino acid
<221> NAME/KEY: MOD_RES
<222> LOCATION: (288)
<223> OTHER INFORMATION: variable or unknown amino acid

<400> SEQUENCE: 5

-continued

```
Met Gln Leu Val Ser Ile Phe Leu Phe Ile Ser Phe Leu Phe Leu Leu
 1               5                  10                  15

Arg Lys Trp Lys Lys Tyr Leu Xaa Xaa Ser Gln Thr Lys Lys Leu Pro
             20                  25                  30

Pro Gly Pro Trp Lys Leu Pro Phe Ile Gln Gly Met Phe His Leu Ala
         35                  40                  45

Gly Gly Leu Pro His His Val Leu Arg Asp Leu Ala Glu Lys Tyr Gly
     50                  55                  60

Pro Leu Met His Leu Gln Leu Gly Glu Val Ser Ala Val Val Val Thr
 65                  70                  75                  80

Ser Pro Met Met Ala Lys Gln Val Leu Lys Thr His Asp Ile Ala Phe
                 85                  90                  95

Ala Ser Arg Pro Lys Leu Leu Ala Met Asp Ile Ile Cys Tyr Xaa Arg
             100                 105                 110

Arg Asp Ile Ala Phe Ser Pro Thr Gly Asp Ile Trp Arg Gln Met Arg
         115                 120                 125

Lys Ile Cys Ile Met Glu Val Leu Ser Ala Lys Ser Val Arg Ser Phe
     130                 135                 140

Ser Ser Ile Arg His Asp Glu Val Val Arg Leu Ile Asp Ser Ile Gln
145                 150                 155                 160

Pro Cys Phe Thr Ser Gln Glu Leu Val Asn Phe Thr Glu Arg Ile Ile
                 165                 170                 175

Trp Phe Thr Ser Ser Met Thr Cys Arg Ser Ala Phe Gly Gln Val Leu
         180                 185                 190

Lys Glu Gln Glu Val Phe Ile Lys Asp Ile Arg Glu Val Ile Ser Leu
     195                 200                 205

Ala Glu Gly Phe Asp Val Ala Asp Ile Phe Pro Ser Tyr Lys Phe Leu
 210                 215                 220

Met Gly Phe Gly Gly Ala Lys Gln Lys Leu Leu Xaa Ala His Arg Lys
225                 230                 235                 240

Val Asp Ser Ile Val Glu Asp Val Ile Lys Glu His Lys Lys Asn Leu
                 245                 250                 255

Ala Thr Arg Lys Ser Asp Asp Ala Ile Gly Gly Glu Asp Leu Val Asp
         260                 265                 270

Ala Leu Val Arg Leu Met Xaa Asp Lys Ser Leu Gln Phe Pro Ile Xaa
     275                 280                 285

Asn Asp Asn Ile Lys Ala Val Ile Ile Asp Leu Phe Ala Ala Gly Thr
 290                 295                 300

Glu Thr Ser Ser Thr Thr Val Trp Ala Trp Ala Met Met Leu Lys
305                 310                 315                 320

Lys Pro Ser Val Phe Ala Lys Ala Gln Ala Lys Val Arg Glu Ala Phe
                 325                 330                 335

Arg Asp Lys Val Thr Phe Asp Lys His Asp Val Glu Glu Leu Lys Tyr
         340                 345                 350

Leu Lys Leu Val Ile Lys Glu Thr Met Arg Leu His Ala Pro Val Pro
     355                 360                 365

Leu Leu Val Pro Arg Glu Cys Arg Glu Glu Thr Glu Ile Asn Gly Thr
 370                 375                 380

Thr Ile Pro Val Lys Thr Lys Val Met Val Asn Val Asn Ala Leu Gly
385                 390                 395                 400

Arg Asp Pro Lys Tyr Trp Asp Asp Ala Glu Ser Phe Lys Pro Glu Arg
                 405                 410                 415

Phe Glu Gln Cys Ser Ile Asp Phe Ile Gly Asn Asn Phe Glu Tyr Leu
```

```
                    420             425             430
Pro Phe Gly Gly Arg Arg Ile Cys Pro Gly Ile Ser Phe Gly Leu
        435                 440             445

Ala Asn Val Tyr Leu Pro Leu Ala Gln Leu Leu Tyr His Phe Asp Trp
    450                 455                 460

Lys Leu Pro Thr Gly Met Glu Pro Lys Asp Leu Asp Leu Thr Glu Ser
465                 470                 475                 480

Ala Gly Ile Thr Ala Ala Arg Lys Gly Asp Leu Tyr Leu Ile Ala Thr
                485                 490                 495

Pro His Gln Pro
            500

<210> SEQ ID NO 6
<211> LENGTH: 504
<212> TYPE: PRT
<213> ORGANISM: Glycine max
<220> FEATURE:
<221> NAME/KEY: MOD_RES
<222> LOCATION: (194)
<223> OTHER INFORMATION: variable or unknown amino acid
<221> NAME/KEY: MOD_RES
<222> LOCATION: (265)
<223> OTHER INFORMATION: variable or unknown amino acid
<221> NAME/KEY: MOD_RES
<222> LOCATION: (280)
<223> OTHER INFORMATION: variable or unknown amino acid
<221> NAME/KEY: MOD_RES
<222> LOCATION: (297)
<223> OTHER INFORMATION: variable or unknown amino acid
<221> NAME/KEY: MOD_RES
<222> LOCATION: (319)
<223> OTHER INFORMATION: variable or unknown amino acid
<221> NAME/KEY: MOD_RES
<222> LOCATION: (428)
<223> OTHER INFORMATION: variable or unknown amino acid
<221> NAME/KEY: MOD_RES
<222> LOCATION: (476)
<223> OTHER INFORMATION: variable or unknown amino acid
<221> NAME/KEY: MOD_RES
<222> LOCATION: (480)
<223> OTHER INFORMATION: variable or unknown amino acid

<400> SEQUENCE: 6

Met Glu Tyr Ser Pro Leu Ser Ile Val Ile Thr Phe Phe Val Phe Leu
 1               5                  10                  15

Leu Leu His Trp Leu Val Lys Thr Tyr Lys Gln Lys Ser Ser His Lys
            20                  25                  30

Leu Pro Pro Gly Pro Trp Arg Leu Pro Ile Ile Gly Met Leu Phe Gln
        35                  40                  45

Leu Ala Leu Ala Ala Ser Leu Pro Asp Gln Ala Ile Gln Lys Leu Val
    50                  55                  60

Arg Lys Tyr Gln Pro Leu Met His Leu Gln Leu Gly Glu Ile Ser Thr
65                  70                  75                  80

Leu Val Val Ser Ser Pro Lys Met Ala Met Glu Met Lys Thr His
                85                  90                  95

Asp Val His Phe Val Gln Arg Pro Gln Leu Leu Ala Pro Gln Phe Met
                100                 105                 110

Val Ile Gly Ala Thr Asp Ile Ala Phe Ala Pro Thr Gly Asp Ile Trp
            115                 120                 125

Arg Gln Ile Arg Lys Ile Cys Ile Leu Glu Leu Leu Ser Ala Lys Arg
        130                 135                 140

Val Gln Ser Phe Ser His Ile Arg Gln Asp Glu Asn Lys Lys Leu Ile
145                 150                 155                 160
```

-continued

```
Gln Ser Ile His Ser Glu Ala Gln Ser Pro Ile Asp Leu Ser Gly Lys
                165                 170                 175
Leu Phe Ser Leu Leu Gly Thr Thr Val Ser Arg Ala Ala Phe Gly Lys
            180                 185                 190
Glu Xaa Asp Asp Gln Asp Glu Phe Met Ser Leu Val Arg Lys Ala Ile
        195                 200                 205
Thr Met Thr Gly Gly Phe Glu Val Asp Asp Met Phe Pro Ser Leu Lys
    210                 215                 220
Pro Leu His Leu Leu Thr Arg Gln Lys Ala Lys Val Glu Met Val Met
225                 230                 235                 240
Gln Arg Ala Asp Lys Ile Leu Glu Asp Ile Leu Arg Lys His Met Glu
                245                 250                 255
Lys Arg Thr Arg Val Lys Glu Gln Xaa Gly Ser Glu Ala Glu Gln Glu
            260                 265                 270
Asp Leu Val Asp Val Leu Leu Xaa Leu Lys Glu Ser Gly Ser Leu Glu
        275                 280                 285
Val Pro Met Thr Met Glu Asn Ile Xaa Ala Val Ile Trp Asn Ile Phe
    290                 295                 300
Ala Ala Gly Thr Asp Thr Ser Ala Ser Thr Leu Phe Trp Ala Xaa Ser
305                 310                 315                 320
Met Met Met Lys Met Pro Lys Val Lys Glu Lys Ala Gln Ala Glu Leu
                325                 330                 335
Arg Gln Ile Phe Lys Gly Lys Glu Ile Ile Arg Lys Thr Asp Leu Glu
            340                 345                 350
Glu Leu Ser Tyr Leu Lys Ser Val Ile Lys Glu Thr Leu Arg Leu Met
        355                 360                 365
Pro Pro Ser Gln Leu Ile Pro Arg Glu Cys Ile Ile Ser Thr Asn Ile
    370                 375                 380
Asp Gly Thr Glu Ile Pro Ile Lys Thr Lys Val Met Ile Asn Thr Trp
385                 390                 395                 400
Ala Ile Gln Arg Asp Pro Gln Tyr Trp Ser Asp Ala Asp Pro Phe Ile
                405                 410                 415
Pro Glu Arg Phe Asn Asp Ser Ser Ile Asp Phe Xaa Gln Asn Ser Thr
            420                 425                 430
Glu Tyr Ile Pro Phe Gly Ala Gly Arg Arg Met Cys Pro Gly Met Thr
        435                 440                 445
Phe Gly Leu Ala Ser Ile Thr Leu Pro Leu Ala Leu Leu Leu Tyr His
    450                 455                 460
Phe Asn Trp Glu Leu Pro Asn Lys Met Lys Pro Xaa Asp Leu Asp Xaa
465                 470                 475                 480
Asp Glu His Phe Gly Met Ile Val Ala Arg Lys Asn Lys Leu Phe Leu
                485                 490                 495
Ile Pro Thr Val Tyr Glu Ala Ser
            500
```

```
<210> SEQ ID NO 7
<211> LENGTH: 502
<212> TYPE: PRT
<213> ORGANISM: Persea sp.
<220> FEATURE:
<221> NAME/KEY: MOD_RES
<222> LOCATION: (1)
<223> OTHER INFORMATION: variable or unknown amino acid
<221> NAME/KEY: MOD_RES
<222> LOCATION: (22)
<223> OTHER INFORMATION: variable or unknown amino acid
```

```
<221> NAME/KEY: MOD_RES
<222> LOCATION: (30)
<223> OTHER INFORMATION: variable or unknown amino acid
<221> NAME/KEY: MOD_RES
<222> LOCATION: (49)
<223> OTHER INFORMATION: variable or unknown amino acid
<221> NAME/KEY: MOD_RES
<222> LOCATION: (199)
<223> OTHER INFORMATION: variable or unknown amino acid
<221> NAME/KEY: MOD_RES
<222> LOCATION: (226)
<223> OTHER INFORMATION: variable or unknown amino acid
<221> NAME/KEY: MOD_RES
<222> LOCATION: (240)
<223> OTHER INFORMATION: variable or unknown amino acid
<221> NAME/KEY: MOD_RES
<222> LOCATION: (247)
<223> OTHER INFORMATION: variable or unknown amino acid
<221> NAME/KEY: MOD_RES
<222> LOCATION: (262)
<223> OTHER INFORMATION: variable or unknown amino acid
<221> NAME/KEY: MOD_RES
<222> LOCATION: (278)
<223> OTHER INFORMATION: variable or unknown amino acid

<400> SEQUENCE: 7

Xaa Ala Ile Leu Val Ser Leu Leu Phe Leu Ala Ile Ala Leu Thr Phe
 1               5                  10                  15

Phe Leu Leu Lys Leu Xaa Glu Lys Arg Glu Lys Lys Pro Xaa Leu Pro
             20                  25                  30

Pro Ser Gly Pro Asn Leu Pro Asp Asp Gly Gly Leu Phe Gln Leu Gly
         35                  40                  45

Xaa Leu Pro His His Ser Leu Arg Ser Leu Ala Met Glu Leu Gln Pro
     50                  55                  60

Leu Ile Leu Asp His Leu Gln His Ile Pro Thr Leu Ile Val Ser Thr
 65                  70                  75                  80

Ala Lys Ile Ala Glu Glu Ile Leu Lys Thr His Asp Leu Ile Phe Ala
                 85                  90                  95

Ser Arg Pro Ser Thr Thr Ala Ala Arg Arg Ile Phe Ile Asp Cys Thr
                100                 105                 110

Asp Val Ala Phe Ser Pro Thr Gly Glu Ile Trp Arg Gln Val Arg Lys
            115                 120                 125

Ile Cys Val Leu Glu Leu Leu Ser Ile Lys Arg Val Asn Ser Tyr Arg
        130                 135                 140

Ser Ile Arg Glu Glu Glu Val Gly Leu Met Met Glu Arg Ile Ser Gln
145                 150                 155                 160

Ser Cys Glu Thr Gln Glu Ala Val Asn Leu Ser Ile Leu Leu Leu Leu
                165                 170                 175

Ile Ser Ser Gly Thr Ile Thr Arg Val Ala Phe Gly Lys Lys Tyr Glu
            180                 185                 190

Gly Glu Glu Arg Lys Xaa Lys Phe Ala Asp Leu Ala Thr Glu Leu
        195                 200                 205

Thr Thr Leu Met Gly Ala Phe Phe Val Gly Asp Tyr Phe Pro Ser Phe
    210                 215                 220

Ala Xaa Val Asp Val Leu Thr Gly Met Asp Ala Arg Leu Lys Arg Xaa
225                 230                 235                 240

His Gly Glu Leu Asp Ala Xaa Val Asp His Val Leu Asp His Leu
                245                 250                 255

Ile Ser Arg Lys Ala Xaa Gly Ser Asp Gly Val Glu Gln Lys Asp Leu
            260                 265                 270

Val Asp Val Leu Leu Xaa Leu Gln Lys Asp Ser Ser Leu Gly Val His
```

```
                275                 280                 285
Leu Asn Arg Asn Asn Leu Lys Ala Val Ile Leu Asp Met Phe Ser Gly
            290                 295                 300

Gly Thr Asp Thr Thr Ser Val Thr Leu Val Trp Ala Leu Ala Met Asp
305                 310                 315                 320

Ile Lys His Pro Asp Val Asn Glu Lys Ala Gln Gln Glu Val Arg Arg
                325                 330                 335

Val Val Gln Lys Lys Ala Lys Val Ile Lys Glu Asp Leu His Gln Leu
            340                 345                 350

His Tyr Leu Lys Leu Ile Ile Lys Glu Thr Leu Arg Asp Met Pro Val
            355                 360                 365

Ala Pro Leu Leu Val Pro Arg Glu Ser Thr Arg Asp Val Val Ile Arg
        370                 375                 380

Gly Thr His Ile Pro Ala Lys Thr Arg Val Phe Ile Asn Ala Asn Ala
385                 390                 395                 400

Ile Gly Arg Asp Pro Lys Ser Trp Glu Asn Ala Glu Glu Phe Leu Pro
                405                 410                 415

Glu Arg Phe Val Asn Asn Ser Val Asp Phe Leu Gly Gln Asp Phe Gln
            420                 425                 430

Ile Ile Pro Arg Gly Ala Gly Arg Arg Gly Cys Pro Gly Ile Ala Phe
        435                 440                 445

Gln Ile Ser Ser Val Glu Ile Ser Leu Ala Asn Leu Leu Tyr Trp Phe
450                 455                 460

Asn Trp Glu Leu Pro Gly Asp Leu Thr Lys Glu Asp Leu Asp Met Ser
465                 470                 475                 480

Glu Ala Val Gly Ile Thr Val His Met Lys Phe Pro Leu Gln Leu Val
            485                 490                 495

Ala Lys Pro His Leu Ser
            500

<210> SEQ ID NO 8
<211> LENGTH: 509
<212> TYPE: PRT
<213> ORGANISM: Nepeta mussinii
<220> FEATURE:
<221> NAME/KEY: MOD_RES
<222> LOCATION: (1)
<223> OTHER INFORMATION: variable or unknown amino acid
<221> NAME/KEY: MOD_RES
<222> LOCATION: (90)
<223> OTHER INFORMATION: variable or unknown amino acid
<221> NAME/KEY: MOD_RES
<222> LOCATION: (113)
<223> OTHER INFORMATION: variable or unknown amino acid
<221> NAME/KEY: MOD_RES
<222> LOCATION: (198)
<223> OTHER INFORMATION: variable or unknown amino acid
<221> NAME/KEY: MOD_RES
<222> LOCATION: (230)
<223> OTHER INFORMATION: variable or unknown amino acid
<221> NAME/KEY: MOD_RES
<222> LOCATION: (254)
<223> OTHER INFORMATION: variable or unknown amino acid
<221> NAME/KEY: MOD_RES
<222> LOCATION: (288)
<223> OTHER INFORMATION: variable or unknown amino acid
<221> NAME/KEY: MOD_RES
<222> LOCATION: (290)
<223> OTHER INFORMATION: variable or unknown amino acid
<221> NAME/KEY: MOD_RES
<222> LOCATION: (319)..(320)
<223> OTHER INFORMATION: variable or unknown amino acid
<221> NAME/KEY: MOD_RES
<222> LOCATION: (468)
```

<223> OTHER INFORMATION: variable or unknown amino acid
<221> NAME/KEY: MOD_RES
<222> LOCATION: (495)
<223> OTHER INFORMATION: variable or unknown amino acid

<400> SEQUENCE: 8

```
Xaa Val Ser Leu Ser Tyr Phe Leu Ile Ala Leu Leu Asp Thr Leu Pro
  1               5                  10                  15

Phe Leu Leu Phe Leu Asn Lys Trp Arg Ser Tyr Ser Gly Lys Thr
             20                  25                  30

Pro Pro Pro Ser Pro Lys Leu Pro Val Ile Gly Gly Leu Phe Gln
             35                  40                  45

Leu Gly Leu Tyr Pro His His Tyr Leu Gln Ser Leu Ser Arg Arg Tyr
 50                  55                  60

Gly Pro Leu Met Gln Leu His Phe Gly Ser Val Pro Val Leu Val Ala
 65                  70                  75                  80

Ser Ser Pro Lys Ala Ala Arg Glu Ile Xaa Lys Asn Gln Asp Ile Val
             85                  90                  95

Phe Ser Asn Arg Pro Lys Met Ser Ile Ala Asn Arg Leu Arg Arg Ala
            100                 105                 110

Xaa Pro Asp Val Ala Phe Thr Gln Thr Gly Glu Ile Trp Arg Gln Ile
            115                 120                 125

Arg Ser Ile Cys Val Leu Gln Leu Leu Ser Leu Lys Arg Val Gln Ser
130                 135                 140

Phe Arg Arg Val Arg Glu Glu Thr Ser Ile Met Val Glu Lys Ile
145                 150                 155                 160

Asn Gln Leu Gly Ser Glu Ser Ser Thr Pro Val Asn Leu Ser Glu Leu
                165                 170                 175

Leu Leu Ser Leu Thr Asn Asp Val Val Cys Arg Val Thr Leu Gly Lys
            180                 185                 190

Lys Tyr Gly Gly Gly Xaa Gly Ser Glu Glu Val Asp Lys Leu Lys Glu
            195                 200                 205

Met Leu Thr Glu Ile Gln Asn Leu Asn Gly Ile Ser Pro Val Trp Leu
            210                 215                 220

Phe Ile Pro Trp Leu Xaa Trp Thr Arg Arg Phe Asp Gln Val Asp Gln
225                 230                 235                 240

Arg Val Asp Arg Ile Val Lys Ala Phe Asp Gly Ile Leu Xaa Ser Val
                245                 250                 255

Ile Gln Glu His Leu Glu Arg Asp Gly Asp Lys Asp Asp Asp Gly Asp
            260                 265                 270

Gly Ala Leu Asp Phe Val Asp Ile Leu Leu Gln Phe Gln Arg Glu Xaa
            275                 280                 285

Lys Xaa Arg Ser Pro Val Glu Asp Asp Thr Val Lys Ala Leu Ile Leu
            290                 295                 300

Asp Met Phe Val Ala Gly Thr Asp Thr Thr Ala Thr Ala Leu Xaa Xaa
305                 310                 315                 320

Ala Val Ala Met Leu Ile Lys Lys Pro Arg Ala Met Lys Arg Leu Gln
                325                 330                 335

Asn Glu Val Arg Glu Val Ala Gln Ser Lys Ala Glu Ile Glu Lys Glu
            340                 345                 350

Asp Leu Glu Lys Met Pro Tyr Leu Lys Ala Ser Ile Lys Glu Ser Leu
            355                 360                 365

Arg Leu His Val Pro Val Val Leu Val Pro Arg Glu Ser Thr Arg
            370                 375                 380
```

```
Asp Thr Asn Val Leu Gly Thr Asp Ile Ala Ser Gly Thr Arg Val Leu
385                 390                 395                 400

Ile Asn Ala Asn Ala Ile Ala Arg Asp Pro Ser Val Trp Glu Asn Pro
            405                 410                 415

Glu Glu Phe Leu Pro Glu Arg Phe Leu Asp Ser Ser Asp Asp Tyr Ile
            420                 425                 430

Gln Leu His Ile Gly Leu Leu Pro Phe Gly Ala Gly Arg Arg Gly Cys
            435                 440                 445

Pro Gly Ala Thr Phe Ala Val Ala Ile Asp Glu Leu Ala Leu Ala Lys
            450                 455                 460

Asp Val Arg Xaa Phe Asp Phe Gly Leu Pro Asn Gly Ala Arg Met Glu
465                 470                 475                 480

Glu Leu Asp Met Ser Glu Thr Ser Gly Met Thr Val His Lys Xaa Ser
            485                 490                 495

Pro Leu Leu Leu Leu Pro Ile Pro His His Ala Ala Pro
            500                 505

<210> SEQ ID NO 9
<211> LENGTH: 504
<212> TYPE: PRT
<213> ORGANISM: Arabidopsis sp.
<220> FEATURE:
<221> NAME/KEY: MOD_RES
<222> LOCATION: (1)
<223> OTHER INFORMATION: variable or unknown amino acid
<221> NAME/KEY: MOD_RES
<222> LOCATION: (62)
<223> OTHER INFORMATION: variable or unknown amino acid
<221> NAME/KEY: MOD_RES
<222> LOCATION: (243)
<223> OTHER INFORMATION: variable or unknown amino acid
<221> NAME/KEY: MOD_RES
<222> LOCATION: (246)
<223> OTHER INFORMATION: variable or unknown amino acid
<221> NAME/KEY: MOD_RES
<222> LOCATION: (253)
<223> OTHER INFORMATION: variable or unknown amino acid
<221> NAME/KEY: MOD_RES
<222> LOCATION: (324)
<223> OTHER INFORMATION: variable or unknown amino acid
<221> NAME/KEY: MOD_RES
<222> LOCATION: (394)
<223> OTHER INFORMATION: variable or unknown amino acid

<400> SEQUENCE: 9

Xaa Val Ser Leu Leu Ser Phe Phe Leu Leu Leu Val Pro Ile Phe
1               5                   10                  15

Phe Leu Leu Ile Phe Thr Lys Lys Ile Lys Glu Ser Lys Gln Asn Leu
            20                  25                  30

Pro Pro Gln Pro Ala Leu Leu Pro Ile Ile Gly Asn Leu Phe Gln Leu
            35                  40                  45

Gln Gly Leu Leu His His Cys Leu His Asp Leu Ser Lys Xaa His Gly
            50                  55                  60

Pro Val Met His Leu Arg Leu Gly Phe Ala Pro Met Val Val Ile Ser
65                  70                  75                  80

Ser Ser Ser Ala Ala Arg Glu Ile Met Lys Asn Gln Asp Ile Val Phe
            85                  90                  95

Ser Asn Arg Pro Lys Met Ser Ile Ala Asn Phe Leu Phe Phe Gly Gly
            100                 105                 110

Lys Asp Ile Gly Phe Gly Val Thr Gly Asp Glu Trp Arg Glu Leu Arg
            115                 120                 125

Lys Leu Ser Val Arg Glu Phe Phe Ser Val Lys Ile Val Gln Ser Phe
```

```
                130                 135                 140
Ile Tyr Ile Arg Glu Glu Glu Asn Asp Leu Met Ile Lys Lys Leu Lys
145                 150                 155                 160

Glu Leu Ala Glu Lys Gln Ser Pro Val Asp Leu Ser Lys Ile Leu Phe
                165                 170                 175

Gly Leu Thr Ala Ser Ile Ile Phe Arg Thr Ala Phe Gly Gln Ser Phe
            180                 185                 190

Phe Asp Asn Lys Met Val Asp Gln Glu Ser Ile Lys Glu Leu Met Phe
            195                 200                 205

Glu Ser Leu Ser Asn Met Thr Phe Arg Phe Ser Asp Phe Phe Pro Thr
        210                 215                 220

Ala Gly Leu Lys Trp Phe Ile Gly Phe Val Ser Gly Gln His Leu Arg
225                 230                 235                 240

Leu Tyr Xaa Val Phe Xaa Arg Val Asp Thr Ile Phe Xaa His Ile Val
                245                 250                 255

Asp Asp His Met Ser Lys Lys Ala Thr Gln Asp Arg Pro Asp Met Val
                260                 265                 270

Asp Ala Ile Leu Asp Met Ile Asp Asn Glu Gln Gln Tyr Ala Ser Phe
            275                 280                 285

Lys Leu Thr Val Asp His Leu Lys Gly Val Leu Ser Asn Ile Tyr His
        290                 295                 300

Ala Gly Ile Asp Thr Ser Ala Ile Ile Leu Ile Trp Ala Leu Ala Met
305                 310                 315                 320

Leu Val Arg Xaa Pro Arg Val His Lys Lys Ala Gln Asp Glu Ile Arg
                325                 330                 335

Thr Cys Ile Gln Ile Lys Gln Glu Gly Arg Ile Met Lys Glu Asp Leu
            340                 345                 350

Asp Lys Leu Gln Tyr Leu Lys Leu Val Val Lys Glu Thr Leu Arg Leu
            355                 360                 365

Met Pro Ala Ala Pro Leu Leu Leu Pro Arg Glu Thr Met Ala Asp Ile
        370                 375                 380

Lys Ile Gln Gly Thr Asp Ile Pro Gln Xaa Arg Ala Leu Leu Val Asn
385                 390                 395                 400

Ala Asn Ser Ile Gly Arg Asp Pro Glu Ser Trp Lys Asn Pro Glu Glu
                405                 410                 415

Phe Asn Pro Glu Arg Phe Ile Asp Cys Pro Val Asp Tyr Leu Gly His
            420                 425                 430

Ser Cys Gln Leu Leu Pro Phe Gly Ser Gly Arg Arg Ile Cys Pro Gly
        435                 440                 445

Ile Ala Met Ala Ile Ala Thr Ile Glu Leu Gly Leu Leu Met Leu Leu
        450                 455                 460

Tyr Phe Phe Asp Trp Asn Met Pro Glu Lys Lys Lys Asp Met Asp Met
465                 470                 475                 480

Glu Glu Ala Gly Asp Leu Ile Val Asp Lys Lys Tyr Pro Leu Glu Leu
                485                 490                 495

Leu Pro Val Ile Arg Ile Ser Leu
            500

<210> SEQ ID NO 10
<211> LENGTH: 509
<212> TYPE: PRT
<213> ORGANISM: Nicotiana sp.
<220> FEATURE:
<221> NAME/KEY: MOD_RES
<222> LOCATION: (32)
```

```
<223> OTHER INFORMATION: variable or unknown amino acid
<221> NAME/KEY: MOD_RES
<222> LOCATION: (107)
<223> OTHER INFORMATION: variable or unknown amino acid
<221> NAME/KEY: MOD_RES
<222> LOCATION: (131)
<223> OTHER INFORMATION: variable or unknown amino acid
<221> NAME/KEY: MOD_RES
<222> LOCATION: (180)
<223> OTHER INFORMATION: variable or unknown amino acid
<221> NAME/KEY: MOD_RES
<222> LOCATION: (197)
<223> OTHER INFORMATION: variable or unknown amino acid
<221> NAME/KEY: MOD_RES
<222> LOCATION: (201)
<223> OTHER INFORMATION: variable or unknown amino acid
<221> NAME/KEY: MOD_RES
<222> LOCATION: (216)
<223> OTHER INFORMATION: variable or unknown amino acid
<221> NAME/KEY: MOD_RES
<222> LOCATION: (220)
<223> OTHER INFORMATION: variable or unknown amino acid
<221> NAME/KEY: MOD_RES
<222> LOCATION: (259)
<223> OTHER INFORMATION: variable or unknown amino acid
<221> NAME/KEY: MOD_RES
<222> LOCATION: (267)
<223> OTHER INFORMATION: variable or unknown amino acid
<221> NAME/KEY: MOD_RES
<222> LOCATION: (271)
<223> OTHER INFORMATION: variable or unknown amino acid
<221> NAME/KEY: MOD_RES
<222> LOCATION: (285)
<223> OTHER INFORMATION: variable or unknown amino acid
<221> NAME/KEY: MOD_RES
<222> LOCATION: (460)
<223> OTHER INFORMATION: variable or unknown amino acid

<400> SEQUENCE: 10

Met Glu Gly Thr Asn Leu Thr Thr Tyr Ala Ala Val Phe Leu Gly Thr
  1               5                  10                  15

Leu Phe Leu Leu Phe Leu Ser Lys Leu Leu Arg Gln Arg Lys Leu Xaa
                 20                  25                  30

Leu Pro Pro Gln Pro Lys Pro Trp Pro Ile Ile Gly Gly Leu Asn Leu
             35                  40                  45

Ile Gly Asn Leu Pro His His Ser Ile His Glu Leu Ser Leu Leu Thr
 50                  55                  60

Gly Pro Val Met Gln Leu Gln Phe Gly Ser Phe Pro Val Val Val Gly
 65                  70                  75                  80

Ser Ser Val Lys Met Ala Ile Ile Phe Leu Thr Ser Met Asp Ile Asn
                 85                  90                  95

Phe Val Gly Arg Pro Lys Thr Ala Ala Gly Xaa Tyr Thr Thr Ile Asp
                100                 105                 110

Tyr Ser Asp Ile Thr Trp Ser Pro Thr Gly Pro Ile Trp Arg Gln Ala
            115                 120                 125

Arg Lys Xaa Cys Leu Thr Glu Leu Phe Ser Thr Lys Cys Leu Asp Ser
        130                 135                 140

Tyr Glu Tyr Phe Arg Ala Glu Glu Leu Asn Ser Leu Leu His Asn Leu
145                 150                 155                 160

Met Lys Ile Ser Gln Lys Pro Ile Val Leu Lys Asp Tyr Leu Thr Thr
                165                 170                 175

Leu Ser Leu Xaa Val Ile Ser Arg Met Val Leu Gly Lys Arg Tyr Leu
            180                 185                 190

Asp Glu Ser Glu Xaa Ser Phe Val Xaa Pro Glu Glu Phe Lys Lys Met
        195                 200                 205
```

```
Leu Asp Glu Leu Phe Leu Leu Xaa Gly Val Leu Xaa Ile Gly Asp Ser
    210                 215                 220

Ile Pro Trp Ile Asp Phe Met Asp Leu Gln Gly Tyr Val Ile Arg Met
225                 230                 235                 240

Lys Val Val Ser Lys Lys Phe Asp Lys Ile Leu Glu His Val Ile Asp
            245                 250                 255

Glu His Xaa Ile Arg Arg Asn Gly Val Glu Xaa Tyr Val Ala Xaa Asp
            260                 265                 270

Met Glu Asp Val Leu Leu Gln Ile Ala Asp Asp Pro Xaa Leu Glu Val
            275                 280                 285

Lys Leu Glu Arg Glu Gly Val Lys Ala Phe Thr Gln Asp Met Leu Ala
    290                 295                 300

Gly Gly Ile Glu Ser Ser Ala Val Thr Val Ile Trp Ala Ile Ser Met
305                 310                 315                 320

Leu Ser Lys Lys Pro Glu Ile Phe Lys Lys Ala Thr Glu Glu Leu Asp
            325                 330                 335

Arg Val Ile Gln Gln Asn Arg Trp Val Gln Lys Lys Asp Ile Pro Lys
            340                 345                 350

Leu Pro Tyr Ile Glu Ala Ile Val Lys Glu Thr Met Arg Leu His Pro
    355                 360                 365

Phe Ala Pro Met Lys Ala Thr Glu Cys Arg Glu Asn Ser Lys Val Ala
    370                 375                 380

Gly Thr Asp Val Gln Lys Gly Thr Arg Val Leu Val Ser Val Asn Thr
385                 390                 395                 400

Ile Gly Arg Asp Pro Thr Leu Trp Asp Glu Pro Glu Val Phe Lys Pro
            405                 410                 415

Glu Arg Phe His Glu Lys Ala Ser Ile Asp Val Leu Gly His Glu Tyr
            420                 425                 430

Gln Leu Leu Pro Pro Gly Val Gly Arg Arg Met Cys Pro Gly Tyr Ser
    435                 440                 445

Leu Gln Leu Lys Val Ile Gln Ala Ser Leu Ala Xaa Leu Leu His Gly
    450                 455                 460

Phe Asn Trp Ser Leu Pro Asp Asn Met Thr Pro Glu Asp Leu Asn Met
465                 470                 475                 480

Asp Glu Ile Phe Gly Leu Ser Thr Pro Lys Lys Phe Pro Leu Ala Thr
            485                 490                 495

Val Ile Glu Pro Pro Leu Ser Pro Lys Leu Thr Ser Thr
            500                 505
```